United States Patent [19]
Hansson

[11] Patent Number: 6,025,540
[45] Date of Patent: Feb. 15, 2000

[54] TRANSGENIC NON-HUMAN MAMMALS PRODUCING EC-SOD PROTEIN IN THEIR MILK

[76] Inventor: Lennart Hansson, Björkvägen 50, S-902 40 Umeå, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/556,965

[22] PCT Filed: Jun. 24, 1994

[86] PCT No.: PCT/IB94/00181

§ 371 Date: Dec. 7, 1995

§ 102(e) Date: Dec. 7, 1995

[87] PCT Pub. No.: WO95/00637

PCT Pub. Date: Jan. 5, 1995

[30] Foreign Application Priority Data

Jun. 24, 1993 [DK] Denmark .................................. 0753/93

[51] Int. Cl.[7] .............................. C12N 5/00; C12N 15/00; A01K 67/00; C12P 21/00
[52] U.S. Cl. ..................................... 800/14; 800/8; 800/4; 800/7; 800/23; 800/25
[58] Field of Search ..................................... 800/2, 8, 4, 7, 800/14, 23, 25; 536/23.1, 23.2, 23.4, 23.5, 24.1; 435/69.1, 69.7, 71.1

[56] References Cited

FOREIGN PATENT DOCUMENTS

| | | |
|---|---|---|
| 87/01387 | 3/1987 | WIPO . |
| 88/10118 | 12/1988 | WIPO . |
| 90/05188 | 5/1990 | WIPO . |
| 91/04315 | 4/1991 | WIPO . |

OTHER PUBLICATIONS

Oury, Tim D. et al., "Cold–induced brain edema in mice: Involvement of extracellular superoxide dismutase and nitric acid." The Journal of Biological Chemistry, vol. 268, No. 21, pp. 15394–15398 (1993).

Oury, Tim D. et al., "Extracellular superoxide dismutase, nitric oxide, and central nervous system $O_2$ toxicity." Proc. Natl. Acad. Sci., vol. 89, pp. 9715–9719 (Oct. 1992).

Hennighausen, Lothar, "The mammary gland as a bioreactor: Production of foreign proteins in milk." Protein Expression and Purification, vol. 1, pp. 3–8 (1990).

Primary Examiner—Scott D. Priebe
Assistant Examiner—Michael C. Wilson
Attorney, Agent, or Firm—Iver P. Cooper

[57] ABSTRACT

The present invention relates to a transgenic non-human mammal comprising a DNA sequence encoding human extracellular superoxide dismutase (human EC-SOD) or a variant thereof which is expressed in the milk. Transgenic mice containing a chimeric whey acidic protein gene promoter operatively linked to human EC-SOD gene were produced. Levels of up to 0.7 mg human EC-SOD protein/mL milk were observed. The mammalian expression system is preferably expressed in a non-human mammal selected from the group containing rabbits, mice, rats, goats, sheep, pigs, llama, camels and bovine species. The human EC-SOD proteins dismutate superoxide radicals and bind heparin. Within the scope of the invention are also method for producing a transgenic non-human mammal capable of expressing human EC-SOD as defined above, and methods of making milk and methods of isolating protein from the milk.

36 Claims, 8 Drawing Sheets

```
                       210              215             220
Native     HisSerGluArgLysLysArgArgArgGluSerGluCysLysAlaAla***
           CACTCAGAGCGCAAGAAGCGGCGGCGCGAGAGCGAGTGCAAGGCCGCCTGA T209       HisSerGlu***
           CACTCAGAGTGAAAGAAGCGGCGGCGCGAGAGCGAGTGCAAGGCCGCCTGA T213       HisSerGluArgLysLysArg***
           CACTCAGAGCGCAAGAAGCGGTGACGCGAGAGCGAGTGCAAGGCCGCCTGA T215       HisSerGluArgLysLysArgArgArg***
           CACTCAGAGCGCAAGAAGCGGCGGCGCTAGAGCGAGTGCAAGGCCGCCTGA T216       HisSerGluArgLysLysArgArgArgGlu***
           CACTCAGAGCGCAAGAAGCGGCGGCGCGAGTGAGAGTGCAAGGCCGCCTGA SA216      HisSerGluArgLysLysArgArgArgAlaSerGluCysLysAlaAla***
           CACTCAGAGCGCAAGAAGCGGCGGCGCGCGAGCGAGTGCAAGGCCGCCTGA SA219      HisSerGluArgLysLysArgArgArgGluSerGluAlaLysAlaAla***
           CACTCAGAGCGCAAGAAGCGGCGGCGCGAGAGCGAGGCCAAGGCCGCCTGA SA220      HisSerGluArgLysLysArgArgArgGluSerGluCysAlaAlaAla***
           CACTCAGAGCGCAAGAAGCGGCGGCGCGAGAGCGAGTGCGCGGCCGCCTGA SA211-213  HisSerGluArgAlaAlaAlaArgArgGluSerGluCysLysAlaAla***
           CACTCAGAGCGCGCGGCGGCGCGGCGCGAGAGCGAGTGCAAGGCCGCCTGA SA216/218  HisSerGluArgLysLysArgArgArgAlaSerAlaCysLysAlaAla***
           CACTCAGAGCGCAAGAAGCGGCGGCGCGCGAGCGCGTGCAAGGCCGCCTGA SA216/220  HisSerGluArgLysLysArgArgArgAlaSerGluCysAlaAlaAla***
           CACTCAGAGCGCAAGAAGCGGCGGCGCGCGAGCGAGTGCGCGGCCGCCTGA SAT216     HisSerGluArgLysLysArgArgArgAla***
           CACTCAGAGCGCAAGAAGCGGCGGCGCGCGTGAGAGTGCAAGGCCGCCTGA SRT216     HisSerGluArgLysLysArgArgArgArg***
           CACTCAGAGCGCAAGAAGCGGCGGCGCCGGTGAGAGTGCAAGGCCGCCTGA
```

Fig. 1

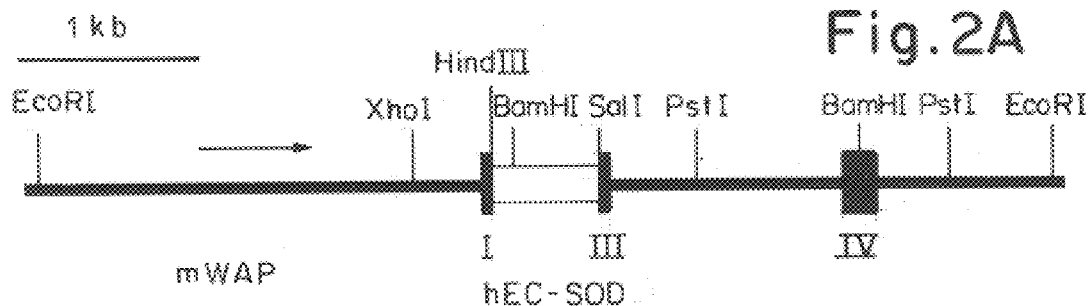
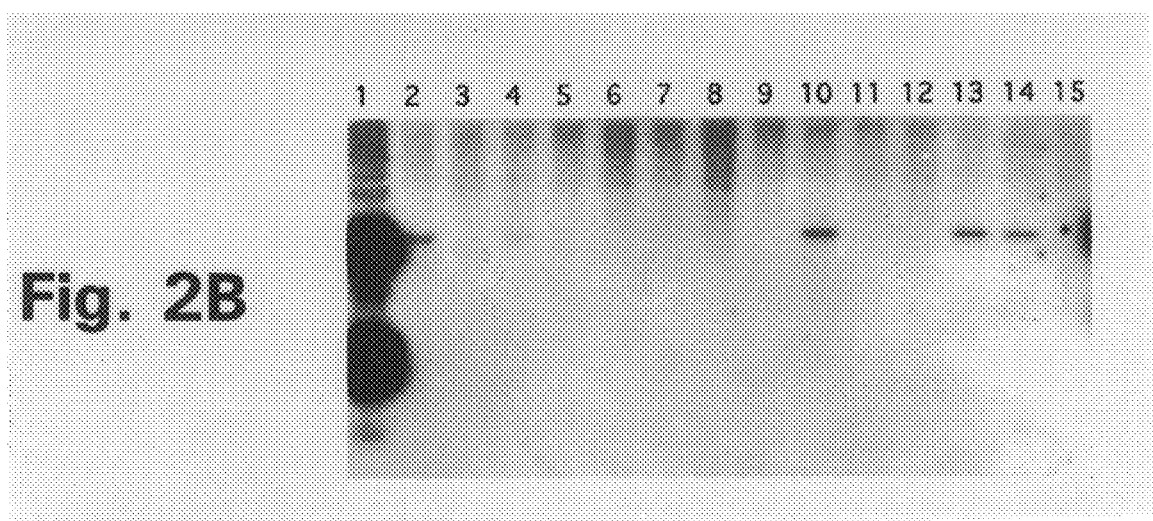

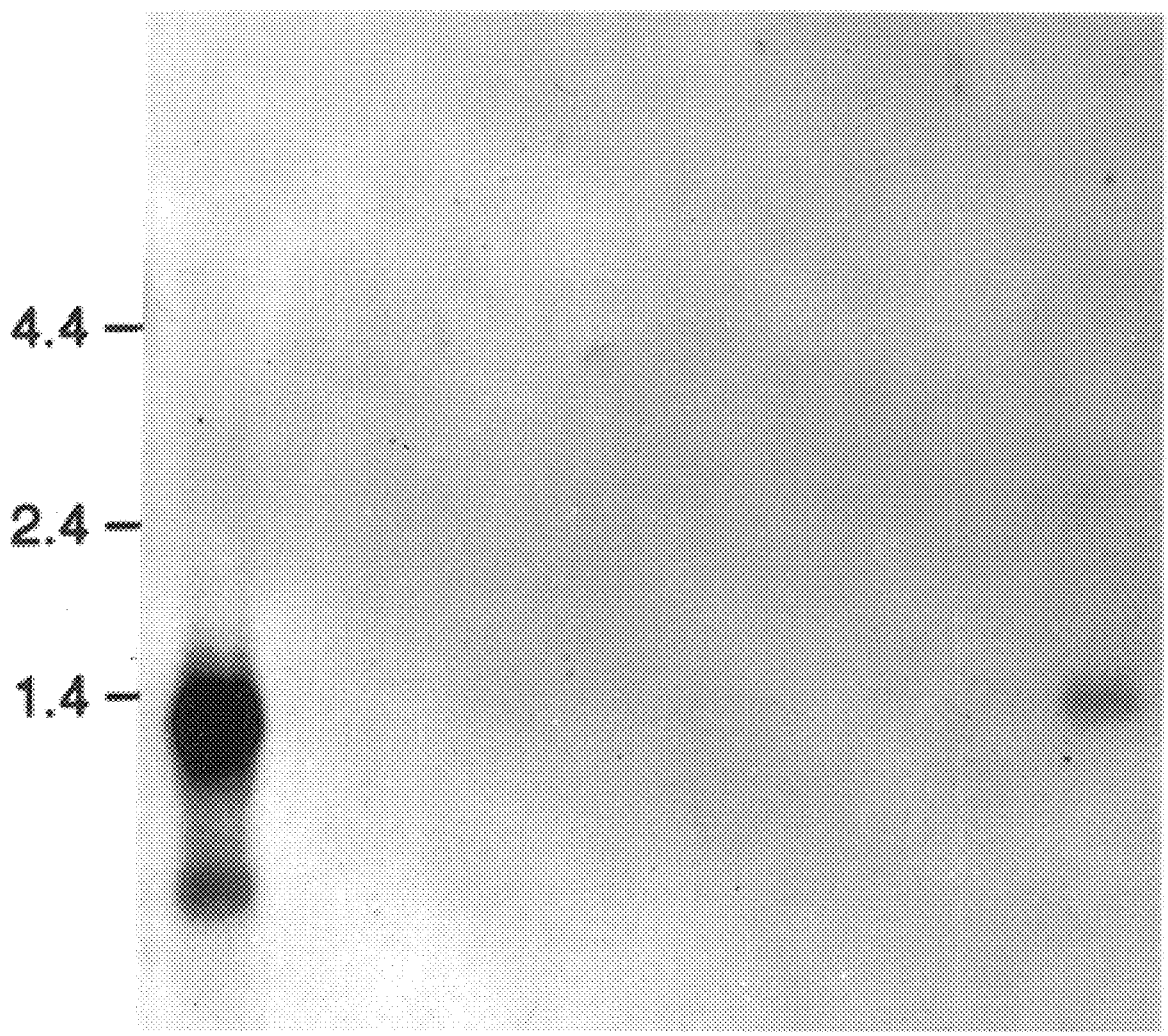

TRANSGENIC NON-HUMAN MAMMALS PRODUCING EC-SOD PROTEIN IN THEIR MILK

This application was filed in the U.S. under 35 U.S.C. §371 by entry into the U.S. national stage of the international (PCT) application, PCT/IB94/00181 filed Jun. 24, 1994.

The present invention relates to a mammalian expression system comprising a DNA sequence encoding human extra cellular superoxide dismutase (EC-SOD) or encoding a variant of said protein having the superoxide dismutating property of native extracellular superoxide dismutase by means of production in transgenic non-human mammals, and to a method of producing a transgenic mammal capable of expressing EC-SOD or a variant thereof. The present invention furthermore relates to a genomic DNA sequence advantageously used in the production of recombinant human EC-SOD or a variant thereof.

Organisms living in the presence of oxygen have been forced to develop a number of protective mechanisms against toxic oxygen reduction metabolites, such as superoxide radicals, which are formed in connection with a variety of biological oxidations. The protective factors include superoxide dismutases (SOD) which dismutate the superoxide radical and are found in relatively constant amounts in mammalian cells and tissue. The secretory extracellular superoxide dismutase (EC-SOD) is one of three different SOD isoenzymes present in mammals [1]. It is the major SOD isoenzyme in plasma, lymph and synovial fluid [2–5], but exists primarily in the interstitial space of tissues [6–8]. The other two isoenzymes are the dimeric CuZn-SOD, which is an intracellular cytosolic enzyme and the tetrameric Mn-SOD, which is found in the mitochondrial matrix [9–11]. The human EC-SOD cDNA has been isolated and sequenced [12] and the recombinant protein has been produced in mammalian cells (WO 87/01387).

The DNA sequence shown in SEQ ID NO:1 is the part of the cDNA sequence corresponding to amino acid residues 1–222. EC-SOD is a secretory protein and the complete cDNA also encodes an 18 amino acids long signal sequence which is absent in mature and recombinant EC-SOD. [12] As deduced from the cDNA sequence, the subunit molecular weight of the mature enzyme is 24,200. The exact size of the carbohydrate substituent is not known, but the apparent molecular weight on gel chromatography is 140–150 kDa. EC-SOD is a tetrameric Cu and Zn containing glycoprotein. On SDS-PAGE electrophoresis the sub-units display a molecular weight of 30–32 kDa. The sequence contains one glycosylation site Asn-89. The tetramers contain 4 Cu and 4 Zn atoms, in that each subunit binds one copper and one zink atom. The active site, which contains the metal atoms, is homologous to the active site of the intracellular CuZn SODs.

The part of the EC-SOD constituting amino acid sequence 1–96 is contemplated to be involved in the formation of oligomers of the polypeptide whereas the part of EC-SOD constituting amino acid sequence 97–193 is contemplated to comprise the active site of the enzyme.

The glycan of the native protein has not been subject for any thorough investigation but the mature enzyme binds to the lectins concanavalin A, wheat germ lectin and lentil lectin. A fundamental and distinguishing property of EC-SOD is its affinity for some glycosaminoglycans such as heparin and heparan sulfate [1, 3, 4, 16, 17]. The latter, which exists in the glycocalyx of cell surfaces and in the connective tissue matrix, is the important physiological ligand of EC-SOD. Because of this affinity, EC-SOD forms in the vasculature an equilibrium between the plasma phase and the glycocalyx of the endothelium [3, 4, 15, 18]. In tissues, virtually all EC-SOD exists anchored to heparan sulfate in the interstitial space and in the cell surfaces [8].

Upon intravenous injection, EC-SOD rapidly binds to the surface of the endothelium and it displays a long half-life (15–20 hours) in the vasculature [8, 15]. When administered parenterally, CuZn-SOD has been shown to exert a host of therapeutic actions [21–25]. The experience with EC-SOD is in comparison small [26–33] but this isoenzyme seems to be even more potent. The high efficacy is apparently related to the special pharmacokinetic properties of the enzyme.

The heparin-binding domain of the enzyme is located to the positively charged carboxyterminal end [19]. This domain is easily proteolysed [20] resulting in vivo in EC-SOD forms with reduced and absent heparin affinities [8].

EC-SOD isolated from tissues and plasma is heterologous with regard to heparin affinity, and can upon chromatography on Heparin-Sepharose be divided into three subclasses;
A which does not bind,
B with intermediate affinity and
C with relatively strong heparin affinity.

In vivo the correlate of the heparin affinity is binding to heparan sulfate proteoglycan, which occurs on cell surfaces and in the interstitial connective tissue.

Upon injection of heparin, bound enzyme is released to plasma because it binds to the heparin instead of the heparan sulfate.

EC-SOD Cs appear to bind to the surface of most cell-types in the body, notable exceptions are erythrocytes and neutrophilic leukocytes. Binding to various *E. coli* strains could not be demonstrated. This binding pattern suggests that EC-SOD C has the potential to protect most normal cells in the body, without protecting microorganisms lacking affinity and without much interfering with superoxide radicals produced at the surfaces of activated neutrophil leukocytes.

In plasma, EC-SOD A and EC-SOD B seem to be quantitatively important, whereas only minor amounts seem to be present in tissue. Studies up till now indicate that in the native environment, especially in the plasma, the three types of EC-SOD are present. In addition, EC-SOD forms an equilibrium between the plasma and endothelial surfaces.

Recombinant EC-SOD has previously been produced in mammalian cells, yeast and bacteria. Cost effective large scale production of recombinant EC-SOD has, however, not yet been possible.

Expression of recombinant genes in transgenic animals and preparation of transgenic animals in general have previously been reported. For example, U.S. Pat. No. 4,736,866 discloses a transgenic mouse containing a c-myc oncogene. Oury et al. [54] report on the generation of a transgenic mouse containing the EC-SOD cDNA under the control of the human β-actin promoter. The transgenic animals in these two disclosures were generated to be used as an animal disease model or for the study of the physiological function of a specific enzyme.

Reports of producion of recombinant proteins in transgenic animals include PCT Publication No. WO 82/04443 (rabbit β-globin gene DNA fragment injected into the pronucleus of a mouse zygote); EPO Publication No. 0 264 166 (Hepatitis B surface antigen and Tissue Plasminogen Activator genes under control of the whey acid protein promoter for mammary tissue specific expression); EPO Publication No. 0 247 494 (transgenic mice containing heterologous DNA encoding various forms of insulin); PCT Publication No. WO 88/00239 (tissue specific expression of DNA encoding factor IX under control of a whey protein promoter); PCT Publication No. WO 88/01648 (transgenic mammal having mammary secretory cells incorporating a recombinant expression system comprising a mammary lactogen-inducible regulatory region and a structural region encoding a heterologous protein); EPO Publication No. 0 279 582 (tissue specific expression of chloramphenicol acetyltransferase under control of rat β-casein promoter in transgenic mice); W091/03551 (production of growth hormone in transgenic animal milk) and WO 91/08216 (production of recombinant polypeptides by bovine species and transgenic methods).

Genetic control elements from different milk protein genes have been used to direct production of recombinant proteins in the milk of transgenic animals [34–36]. The use of such transgenic techniques in farm animals offers the potential to produce pharmaceutical proteins in the milk.

Despite the fact that many cDNAs and genomic fragments now have been evaluated in mammary gland expression systems in transgenic animals, it is hard to define the factors that affect the level of expression. Limited attention has been focused on the qualitative aspects related to detailed analysis of post-translational modifications of recombinant proteins produced by this route; and production of an enzymatic functional multimeric metalloprotein in milk from a transgenic animal, where the function of the protein is closely related to the posttranslational modification, has not been described.

BRIEF DESCRIPTION OF THE INVENTION

It is an object of the invention to provide a means for producing recombinant human EC-SOD in a high yield.

Accordingly, in one aspect the present invention relates to a mammalian expression system comprising a DNA sequence encoding a polypeptide having the amino acid sequence shown in SEQ ID NO:2 or a variant thereof which has a biological activity of human EC-SOD said DNA sequence is combined with regulatory element of a gene encoding a milk protein of a mammal so as to form a hybrid gene which is expressible in the mammary gland of an adult female of a non-human mammal harbouring said hybrid gene so that the polypeptide encoded by the DNA sequence is produced when the hybrid gene is expressed.

In another aspect the present invention relates to a DNA fragment comprising a DNA sequence encoding a polypeptide comprising the amino acid sequence shown in SEQ ID NO:2 and further comprising at least one intron sequence or a variant of said DNA sequence which
1) hybridizes with the DNA sequence shown in SEQ ID NO:1 or a specific part thereof, preferably under the stringent hybridization conditions or
2) encodes a polypeptide, the amino acid sequence of which is at least 85% homologous with the amino acid sequence shown in in SEQ ID NO:2, or
3) constitutes an effective subsequence of said DNA sequence,
and encodes a polypeptide having the biological activity of human EC-SOD.

The stringent hybridization conditions referred to above are to be understood in their conventional meaning, i.e. that hybridization is carried out at 67° C. in 2×SSC and final washing at 67° C. in 1×SSC using the method specified in the "Definition" part of the Examples below.

The term "homologous" is used here to illustrate the degree of identity between the amino acid sequence of a given polypeptide and the amino acid sequence shown in in SEQ ID NO:2. The amino acid sequence to be compared with the amino acid sequence shown in SEQ ID NO:2 may be deduced from a DNA sequence, e.g. obtained by hybridization as defined above, or may be obtained by conventional amino acid sequencing methods. The degree of homology is preferably determined on the amino acid sequence of a mature polypeptide, i.e. without taking any leader sequence into consideration. It is preferred that the degree of homology is at least 85%, such as at least 90%, preferably at least 95% or even 98% with the amino acid sequence shown in SEQ ID NO:2.

The term "effective subsequence" as used above refers to a subsequence which encodes a peptide being functional with respect to the activity of human EC-SOD as defined in the following. The subsequence may be the result of a truncation at either end of the DNA sequence or of the removal of one or more nucleotides or nucleotide sequences within DNA sequence.

The term "a biological activity" of human EC-SOD should be understood as the superoxide dismutating activity of EC-SOD.

The peptide encoded by the subsequence may have heparin affinity which is similar to, increased or decreased as compared to the heparin affinity of human EC-SOD type C.

In the present context, the term "heparin affinity which is similar to, increased or decreased as compared to the heparin affinity of human EC-SOD type C" indicates the polypeptide either has the same, or a less strong or stronger binding to heparin under physiological conditions than the binding of recombinant EC-SOD type C, the binding being assessed in vitro by elution with NaCl as described in the Examples below. Thus, the heparin affinity is determined by means of the concentration of NaCl required for eluting the polypeptide when bound to heparin.

In yet a further aspect, the present invention relates to a method of producing a transgenic non-human mammal capable of expressing a recombinant polypeptide of the invention, comprising injecting a mammalian expression system as defined above into a fertilized egg or a cell of an embryo of a mammal so as to incorporate the expression system into the germline of the mammal and developing the resulting injected fertilized egg or embryo into an adult female mammal.

A transgenic cell or animal contains one or more transgenes within its genome. A transgene is a DNA sequence integrated at a locus of a genome, wherein the transgenic DNA sequence is not otherwise normally found at that locus in that genome.

Transgenes may be made up of heterologous DNA sequences (sequences normally found in the genome of other species) or homologous DNA sequences (sequences derived from the genome of the same species).

As used herein, a "recombinant polypeptide" (or the recombinant DNA sequence encoding the same) is a "heterologous polypeptide". Heterologous polypeptides are polypeptides which are not normally produced by the transgenic animal.

Each of the heterologous or homologous polypeptides are characterized by specific amino acid and nucleic acid sequences. It is to be understood, however, that such sequences include naturally occurring allelic variations thereof and variants produced by recombinant methods wherein such nucleic acid and polypeptide sequences have been modified by substitution, insertion and/or deletion of one or more nucleotides in said nucleic acid sequences to cause the substitution, insertion or deletion of one or more amino acid residues in the recombinant polypeptide. When the term DNA is used in the following, it should be understood that for the number of purposes where DNA can be substituted with RNA, the term DNA should be read to include RNA embodiments which will be apparent for the man skilled in the art.

In further aspects, the present invention relates to a replicable expression vector which carries and is capable of expressing such DNA sequence, a cell harbouring such a vector, a method for producing the polypeptide, a transgenic animal per se, milk from such a transgenic animal.

DETAILED DESCRIPTION OF THE PRESENT INVENTION

Figure 3B:
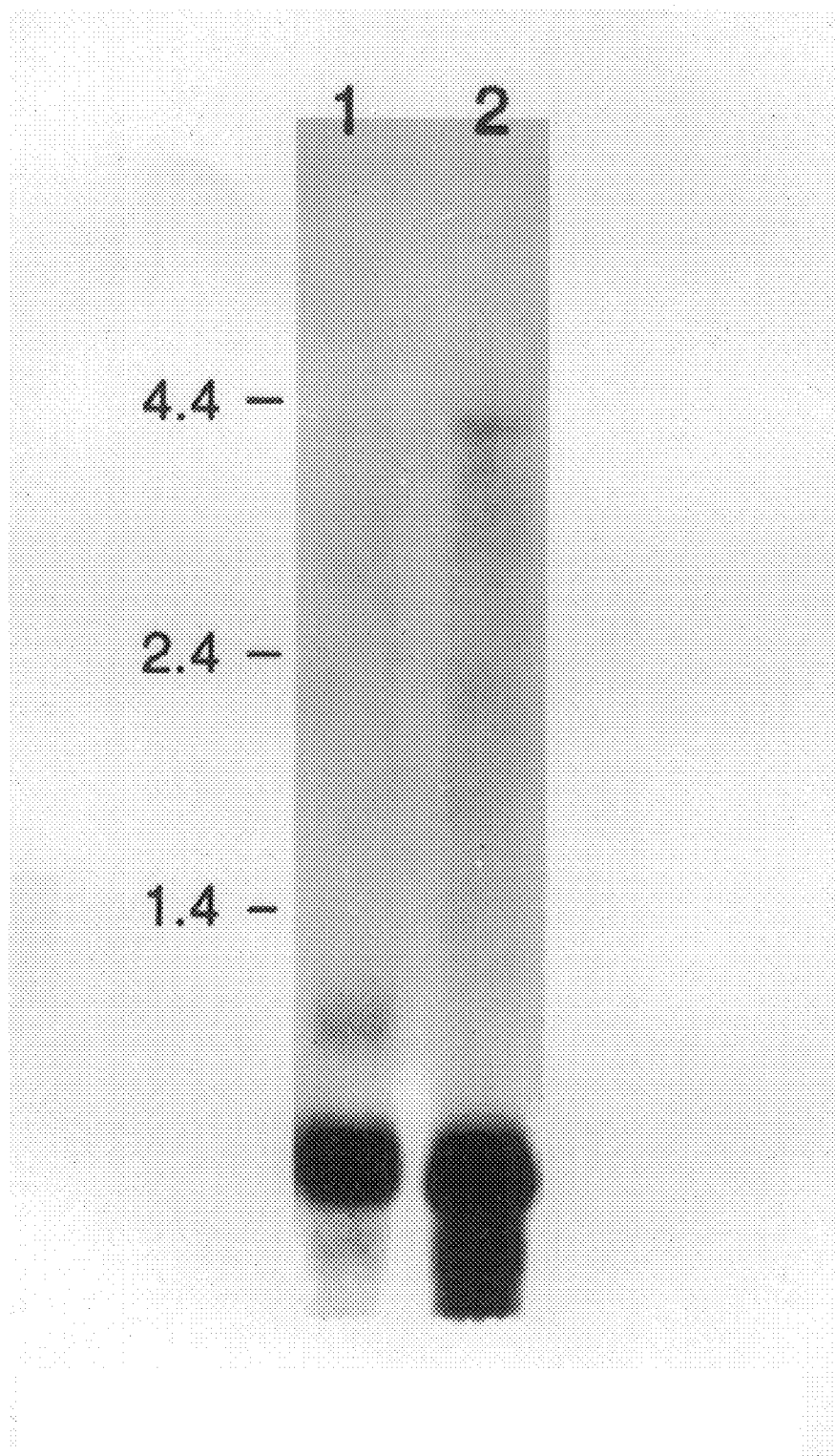

The mammalian expression system according to the invention may be an expression system comprising a DNA sequence encoding a polypeptide having the amino acid sequence shown in SEQ ID NO:2 or a variant thereof which has a biological activity of human EC-SOD, said DNA sequence is combined with regulatory element of a gene encoding a milk protein of a mammal so as to form a hybrid gene which is expressible in the mammary gland of an adult female of a non-human mammal harbouring said hybrid gene so that the polypeptide encoded by the DNA sequence is produced when the hybrid gene is expressed.

As discussed in detail in the following, the expression system according to the invention is, for many purposes, preferably an expression system in which the DNA sequence contains at least one intron sequence, and, preferably, contains at least one permissive RNA splice signal.

As an example, the gene encoding the milk protein may be one selected from whey acidic protein (WAP) genes, β-lactoglobulin genes or casein genes. The present invention also comprises the hybrid gene as such.

As mentioned above, the expression system is preferably one wherein the variant of the polypeptide encoded is at least 85% homologous with the amino acid sequence shown in SEQ ID NO:2. Another way of expressing the close structural relationship with the DNA sequence shown in SEQ ID NO:1 is to refer to hybridization: The expression system is preferably such that the DNA sequence encoding the polypeptide is one which hybridizes with the DNA sequence in SEQ ID NO:1 or a part thereof, preferably under stringent hybridization conditions as described in the examples.

An interesting embodiment comprises a modified DNA sequence which differs from the DNA sequence defined above in that at least one nucleotide has been deleted, substituted or modified or at least one additional nucleotide has been inserted so as to result in a DNA sequence which encodes a polypeptide having a biological activity of human EC-SOD.

In another aspect, the present invention relates to a DNA fragment comprising a DNA sequence encoding a polypeptide having the amino acid sequence shown in SEQ ID NO:2 or variant thereof which has a biological activity of human EC-SOD, said DNA sequence comprising at least one intron sequence.

The DNA sequence is preferably one which
1) hybridizes with the DNA sequence shown in SEQ ID NO:1 or a specific part thereof, preferably under stringent hybridization conditions or
2) encodes a polypeptide, the amino acid sequence of which is at least 85% homologous with the amino acid sequence shown in SEQ ID NO:2, or
3) constitutes an effective subsequence of said DNA sequence.

In another embodiment the DNA fragment contains at least one permissive RNA splice signal.

In a preferred embodiment, the DNA fragment comprises substantially the DNA sequence shown in SEQ ID NO:1.

Alternatively, the DNA sequence may be a modified DNA sequence which differs from a DNA sequence as defined above in that at least one nucleotide has been deleted, substituted or modified or at least one additional nucleotide has been inserted so as to result in a DNA sequence which encodes a polypeptide having heparin affinity which is similar to, increased or decreased as compared to the heparin affinity of human EC-SOD, such as a variant selected from the group consisting of variants T216, T215, T213, T209, SAT216, SRT216, SA219, SA220, SA211–213, SA216, SA216/218 and SA216/220. The C-terminal sequences of these variants, where the differences are, are shown in FIG. 1 and the sequence listing.

In the present context, the term "gene" is used to indicate a DNA sequence which is involved in producing a polypeptide chain and which includes regions preceding and following the coding region (5'-upstream and 3'-downstream sequences) as well as intervening sequences, the so-called introns, which are placed between individual coding segments (so-called exons) or in the 5'-upstream or 3'-downstream region. The 5'-upstream region comprises a regulatory sequence which controls the expression of the gene, typically a promoter. The 3'-downstream region comprises sequences which are involved in termination of transcription of the gene and optionally sequences responsible for polyadenylation of the transcript and the 3' untranslated region.

The above mentioned regulatory or expression regulation sequences in addition to controlling transcription also contribute to RNA stability and processing, at least to the extent they are also transcribed.

Such expression regulation sequences are chosen to produce tissue-specific or cell type-specific expression of the recombinant DNA. Once a tissue or cell type is chosen for expression, 5' and optional 3' expression regulation sequences are chosen. Generally, such expression regulation sequences are derived from genes that are expressed primarily in the tissue or cell type chosen. Preferably, the genes from which these expression regulation sequences are obtained are expressed substantially only in the tissue or cell type chosen, although secondary expression in other tissue and/or cell types is acceptable if expression of the recombinant DNA in the transgene in such tissue or cell type is not detrimental to the transgenic animal. Particularly preferred expression regulation sequences are those endogenous to the species of animal to be manipulated. However, expression regulation sequences from other species such as those from human genes may also be used. In some instances, the expression regulation sequences and the structural DNA sequences (either genomic or cDNA) are from the same species, e.g. each from bovine species or from a human source. In such cases, the expression regulation sequence and the DNA sequence are homologous to each other. Alternatively, the expression regulation sequences and DNA sequences (either cDNA or genomic) are obtained from different species, e.g. an expression regulation sequence from bovine species and a DNA sequence from a human source. In such cases, the expression regulation and DNA sequence are heterologous to each other. The following defines expression regulation sequences from endogenous genes. Such definitions are also applicable to expression regulation sequences from non-endogenous, heterologous genes.

In general, the 5' expression regulation sequence includes the transcribed portion of the endogenous gene upstream from the translation initiation sequence (the 5' untranslated region or 5' UTR) and those flanking sequences upstream therefrom which comprise a functional promoter. As used herein, a "functional promoter" includes those necessary untranscribed DNA sequences which direct the binding of RNA polymerase to the endogenous gene to promote transcription. Such sequences typically comprise a TATA sequence or box located generally about 25 to 30 nucleotides from the transcription initiation site. The TATA box is also sometimes referred to as the proximal signal. In many instances, the promoter further comprises one or more distal signals located upstream from the proximal signal (TATA box) which are necessary to initiate transcription. Such promoter sequences are generally contained within the first 100 to 200 nucleotides located upstream from the transcription initiation site, but may extend up to 500 to 600 nucleotides or more from the transcription initiation site. Such sequences are either readily apparent to those skilled in the art or readily identifiable by standard methods. Such promoter sequences alone or in combination with the 5' untranslated region are referred to herein as "proximal 5' expression regulation sequences".

In addition to such proximal 5' expression regulation sequences, it is preferred that additional 5' flanking sequences (referred to herein as "distal 5' expression regulation sequences") also be included in the transgene. Such distal 5' expression regulation sequences are believed to contain one or more enhancer and/or other sequences which facilitate expression of the endogenous gene and as a consequence facilitate the expression of the structural DNA sequence operably linked to the distal and proximal 5' expression regulation sequences. These 5' expression regulation sequences regulate the spatial and temporal distribution of gene expression. The amount of distal 5' expression regulation sequences depends upon the endogenous gene from which the expression regulation sequences are derived. In general, however, such sequences comprise 5' flanking regions of approximately 1 kb, more preferably 16 kb and most preferably about 30 kb of 5' flanking sequence. The determination of the optimal amount of distal 5' expression regulation sequences used from any particular endogenous gene is readily determined by varying the amount of distal 5' expression regulation sequence to obtain maximal expression. In general, the distal 5' expression regulation sequence will not be so large as to extend into an adjacent gene and will not include DNA sequences which adversely effect the level of transgene expression.

In addition, it is preferred that 3' expression regulation sequences also be included to supplement tissue or cell-type specific expression. Such 3' expression regulation sequences include 3' proximal and 3' distal expression regulation sequences from an appropriate endogenous gene. The 3' proximal expression regulation sequences include transcribed but untranslated DNA positioned downstream from the translation stop signal in the recombinant DNA sequence (also referred to as the 3' untranslated region or 3' UTR). Such sequences generally terminate at a polyadenylation sequence (either from the endogenous gene or from other sources such as SV40) and sequences that may affect RNA stability. Generally, 3' UTR's comprise about 100 to 1000 nucleotides or more downstream from the translation stop signal in the gene from which the 3' regulation sequence is derived. Distal 3' expression regulation sequences include flanking DNA sequences downstream from the proximal 3' expression regulation sequence. Some of these distal sequences are transcribed, but do not form part of the mRNA while other sequences in this 3' distal expression regulation sequence are not transcribed at all. Such distal 3' expression regulation sequences are believed to contain enhancer and/or other sequences which enhance expression. Such sequences are believed to be necessary for efficient polyadenylation and contain transcription termination sequences. Preferably, such sequences comprise about 2 kb, more preferably 8 kb and most preferably about 15 kb of 3' flanking sequence.

Although the use of both 5' and 3' expression regulation sequences are preferred, in some embodiments of the invention, endogenous 3' regulation sequences are not used. In such cases, the 3' proximal expression regulation sequences normally associated with the genomic DNA encoded by the recombinant DNA sequence are used to direct polyadenylation. In addition, distal 3' regulation sequences from the genomic DNA encoding the recombinant polypeptide may also be employed preferably in the same amounts as set forth for endogenous 3' expression regulation sequences. In such cases, it is to be understood that the recombinant polypeptide encoded by the transgene may comprise either genomic DNA or a double stranded DNA derived from cDNA. As with the 5' expression regulation sequences, the optimal amount of 3' expression regulation sequence may be readily determined by varying the amount of 3' flanking sequence to obtain maximal expression of the recombinant polypeptide. In general, the distal 3' regulation sequence, be it from an endogenous gene or a heterologous gene, will not extend into the adjacent gene from which it is derived and will exclude any sequences which adversely effect the level of transgene expression.

In addition to the 5' and 3' expression regulation sequences and the recombinant DNA (either genomic or derived from cDNA) the transgenes of the invention may also comprise an intron sequence which interrupts the transcribed region of the transgene. Recombinant intervening sequences may, however, also comprise a "hybrid intervening sequence". Such hybrid intervening sequences comprise a 5' RNA splice signal and 3' RNA splice signal from intervening sequences from heterologous or homologous sources.

Such hybrid intervening sequences containing permissive RNA splice signals are preferably used when the recombinant DNA corresponds to a cDNA sequence.

Based on the foregoing, it is apparent that preferred transgenes include large amounts of 5' and 3' expression regulation sequences. Further, the recombinant DNA is preferably derived from genomic clones which may be tens to hundreds of kilobases in length. Based on the present technology for cloning and manipulating DNA, the construction and micro-injection of transgenes is practically limited to linearized DNA having a length not greater than about 50 kb. However, the transgenes of the invention, especially those having a length greater than about 50 kb, may be readily generated by introducing two or more overlapping fragments of the desired transgene into an embryonal target cell. When so introduced, the overlapping fragments undergo homologous recombination which results in integration of the fully reconstituted transgene in the genome of the target cell. In general, it is preferred that such overlapping transgene fragments have 100% homology in those regions which overlap. However, lower sequence homology may be tolerated provided efficient homologous recombination occurs. If non-homology does exist between the homologous sequence portions, it is preferred that the non-homology not be spread throughout the homologous sequence portion but rather be located in discrete areas.

Although as few as 14 base pairs at 100% homology are sufficient for homologous recombination in mammalian cells [55], longer homologous sequence portions are preferred, e.g. 500 bp, more preferably 1000 bp, next most preferably 2000 bp and most preferably greater than 2000 bp for each homologous sequence portion.

When the transgene of the invention encodes a recombinant polypeptide that is encoded by recombinant DNA derived from or corresponding to genomic DNA (or comprised substantially of such genomic sequences, e.g. greater than about 50%, more preferably grater than about 75%, most preferably greater than 90% of the codons encoding the recombinant polypeptide are from genomic sequences), the molar concentrations and protein levels in transgenic milk are the same as for cDNA or higher. In general, the molar concentration of the recombinant polypeptide in such transgenic milk is preferably greater than about 50 $\mu$M, more preferably greater than about 150 $\mu$M, most preferably greater than about 500 $\mu$M.

The foregoing molar concentration and protein levels in bovine transgenic milk will vary depending upon the molecular weight of the particular recombinant polypeptide. A particular advantage of producing a recombinant polypeptide in transgenic milk is that relatively large molecular weight polypeptides may be so produced which are otherwise difficult to produce in large quantities in other systems such as prokaryotic expression systems.

The mouse, however, normally produces between 55 to 80 milligrams of protein per ml of milk, and a rabbit produces about 100 milligrams of protein per ml of milk. A cow, on the other hand, normally produces between 30 to 34 milligrams of protein per ml. Since exceptionally high levels of recombinant polypeptide production may adversely affect the production of endogenous milk protein and/or have adverse effects upon the mammary secretory gland, it is preferred that the recombinant polypeptide concentration be between about 1 and 50% of the normal milk protein concentration, more preferably between 10 to 20% and most preferably between 10 and 15% of the normal amount of protein produced in bovine milk. Such preferred ranges also provide a preferred maximum limit to the aforementioned levels of protein produced in transgenic bovine milk.

The term "effective subsequence" of the gene is to be understood in the same manner as defined above in connection with the DNA sequence.

The hybridization may be carried out as described in the "Definition" part of the Examples below, preferably on the basis of a probe comprising the coding part of the DNA sequence shown in the SEQ ID NO:1 below. The terms "homologous" and "effective subsequences" are used in a similar manner as that defined above.

Preferably, the polypeptide encoded by the variant of the DNA sequence is at least 90% homologous, such as at least 95% or even 98% homologous with the amino acid sequence shown in SEQ ID NO:2.

Examples of specific variants of the DNA sequence of the invention are DNA sequences which comprises an essential part of or the complete DNA sequence shown in SEQ ID NO:1 particularly adapted for expression in a transgenic animal. This DNA sequence is one which, when inserted in the expression system together with suitable regulatory sequences, results in the expression of a polypeptide having the amino acid sequence shown in SEQ ID NO:2 or a variant or a subsequence thereof.

As mentioned above, the DNA sequence shown in SEQ ID NO:1 encodes a polypeptide comprising the functional domain/domains of human EC-SOD. While the presence of a signal peptide in most cases is a prerequisite for allowing the polypeptide expressed from the DNA sequence to be transported out of the cell in which it is produced, the nature and origin of the particular signal peptide to be used may vary and need not be the signal peptide naturally associated with the human EC-SOD.

Native human EC-SOD is glycosylated at asparagine at position 89. It is contemplated that an EC-SOD variant comprising more residues which are glycosylated than the native EC-SOD will have a higher heparin affinity than the native EC-SOD.

The glycosylation of a recombinant polypeptide is dependent of the selected expression system. It is well known that eukaryotic cells of different species and/or tissue origin show variation in the glycosylation machinery. Thus, to achieve the glycosylation modifications of interest, it is critical to select a host organism for the production of the recombinant molecule, which have the capacity to perform the appropriate post-translational glycosylation modifications.

However, there are methods available that allow the modification of the glycosylation machinery of a host organism. This can be done by altering the genome of the host organism, for example a host cell or a transgenic animal, by introduction of recombinant genetic elements. These genetic elements can either encode additional or modified glycosyltransferases or other involved enzymes, and mediate their expression, or inhibit the function of endogenous glycosyltransferases or other involved enzymes. Inhibition can be achieved by knocking-out endogenous glycosyltransferase gene functions or by introduction of vectors encoding RNA sequences which are complementary to endogenous glycosyltransferase mRNA species, thereby function as antisense RNA.

The polypeptide encoded by the modified DNA sequence has normally an amino acid sequence which is different from the amino acid sequence of the human EC-SOD.

When "substitution" is performed, one or more nucleotides in the full nucleotide sequence are replaced with one or more different nucleotides; when "addition" is performed, one or more nucleotides are added at either end of the full nucleotide sequence; when "insertion" is performed one or more nucleotides within the full nucleotide sequence is inserted; and when "deletion" is performed one or more nucleotides are deleted from the full nucleotide sequence whether at either end of the sequence or at any suitable point within it.

A modified DNA sequence may be obtained by wellknown methods, e.g., by use of site-directed mutagenesis.

An example of an important modified DNA sequence of the invention is a DNA sequence in which additional codons encoding asparagine residues have been inserted so as to result in a modified DNA sequence encoding a polypeptide having an increased number of residues to be glycosylated. The additional residues may be inserted either by being added at either end or within a DNA sequence of the invention or by replacing one or more non-asparagine codons present in a DNA sequence of the invention. A polypeptide encoded by such a modified DNA sequence is contemplated to have a higher degree of glycosylation.

Another example of interesting modified DNA sequences are DNA sequences encoding variants of EC-SOD having a reduced heparin affinity as compared to recombinant EC-SOD type C. Such variants may be variants selected from the group consisting of variants T216, T215, T213, T209, SAT216, SRT216, SA219, SA220 and SA211–213 (see FIG. 1 and the sequence listing wherein sequences SEQ ID NOS: 8–15, 18–23 and 28–31 show the C-terminal sequences of these variants).

Further examples of interesting modified DNA sequences are DNA sequences encoding variants of EC-SOD having an increased heparin affinity as compared to recombinant EC-SOD type C. Such variants may be variants selected from the group consisting of variants SA216, SA216/218 and SA216/220. The C-terminal sequences of these variants are shown as SEQ ID NOS: 16–17, 24–25 and 26–27, respectively.

For the purpose of preparing modified DNA sequences, site-directed mutagenesis may be carried out using specific oligonucleotide probes conferring an exchange/removal of the relevant amino acids residues.

The DNA sequences used in the mammalian expression system of the invention explained herein may comprise natural as well as synthetic DNA sequences, the natural sequence typically being derived directly from cDNA or genomic DNA, normally of mammalian origin, e.g. as described below. A synthetic sequence may be prepared by conventional methods for synthetically preparing DNA molecules. Of course, also the DNA sequence may be of mixed cDNA and genomic, mixed cDNA and syntheticDNA, and mixed genomic DNA and synthetic DNA origin. Also RNA sequences may be used as described above.

The terms "sequence", "subsequence", "variant" and "polypeptide" as used herein with respect to sequences, subsequences, variants and polypeptides according to the invention should of course be understood as not comprising these phenomena in their natural environment, but rather fragments, e.g., in isolated, purified, in vitro or recombinant form. When reference is made to a DNA sequence of the invention this should be understood to include "variants", "subsequences" and "modified sequences" as defined above. The term "subsequence" is to be understood as a part of a longer sequence, in the present context as a part of the sequences shown in e.g. SEQ ID NO:1 or 2. Similarly, when reference is made to "a polypeptide of the invention", this should be understood to include any of the polypeptides defined herein.

In a further aspect, the present invention relates to a replicable expression vector which carries and is capable of mediating the expression of a DNA sequence encoding human EC-SOD.

In the present context, the term "replicable" means that the vector is able to replicate in a given type of host cell into which it has been introduced. Immediately upstream of the human EC-SOD DNA sequence there may be provided a sequence coding for a signal peptide, the presence of which ensures secretion of the human EC-SOD expressed by host cells harbouring the vector. The signal sequence may be the one naturally associated with the human EC-SOD DNA sequence or of another origin.

The vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication; examples of such a vector are a plasmid, phage, cosmid, mini-chromosome or virus. Alternatively, the vector may be one which, when introduced in a host cell, is integrated in the host cell genome and replicated together with the chromosome(s) into which it has been integrated. The vector of the invention may carry any of the DNA sequences of the invention as defined above and be used for the expression of any of the polypeptides of the invention defined above.

The present invention thus also relates to a replicable expression vector designated pS 172 which has been deposited on Jun. 7, 1993 with the collection of Deutsche Sammlung von Mikroorganismen und Zellkulturen GmbH (DSM) under the accession number DSM 8335 in accordance with the provisions of the Budapest Treaty, and expression vectors expressing DNA sequences which differ from the DNA sequences of the said deposited expression vector, but which code for the same polypeptide or a variant thereof which has a biological activity of human EC-SOD as well as a replicable expression as defined above, wherein the DNA sequence expressed is one which differs from the DNA sequence of the deposited vector in that at least one nucleotide has been deleted, substituted or modified or at least one additional nucleotide has been inserted so as to result in a DNA sequence which encodes a polypeptide having a biological activity of EC-SOD.

The present invention further relates to a cell harboring a replicable expression vector as defined above. In principle, this cell may be of any type of cell, i.e. a prokaryotic cell such as a bacterium, e.g. *E. coli*, a unicellular eukaryotic organism, a fungus or yeast, e.g. *Saccharozyces cerevisiae* or a cell derived from a multicellular organism, e.g. a mammal. The mammalian cells are especially suitable for the purpose and are further discussed below.

In another important aspect, the invention relates to a method of producing recombinant human EC-SOD, said method comprising introducing at least one expression system as defined above into the genome of an non-human mammal in such a way that the DNA encoding the polypeptide is expressed in a mammary gland of the non-human mammal, collecting the milk secreted from the gland, and recovering the recombinant polypeptide from the milk, optionally followed by purification. A suitable vector may be any of the vectors described above, and an appropriate host cell may be any of the cell types listed above. The methods employed to construct the vector and affect introduction thereof into the host cell may be any methods known for such purposes within the field of recombinant DNA.

In one embodiment 1–10 copies of the expression system or a subsequence thereof are injected, in another 1–7 copies of the expression system or a subsequence thereof are injected.

The copies of the expression system or of a subsequence thereof may either be identical or comprise different DNA sequences resulting in expression of at least two different variants of EC-SOD, resulting in heterologous tetramers of EC-SOD in the milk. The variants may have the same heparin affinity or differ with respect to heparin affinity.

In order to be secreted, the DNA sequence encoding human EC-SOD should be preceded by a sequence encoding a signal peptide, the presence of which ensures secretion of human EC-SOD from the cells so that at least a significant proportion of the human EC-SOD expressed is secreted, and may be recovered.

The mammary gland as a tissue of expression and genes encoding milk proteins are generally considered to be particularly suitable for use in the production of heterologous proteins in transgenic non-human mammals as milk proteins are naturally produced at high expression levels in the mammary gland. Also, milk is readily collected and available in large quantities.

In the present context the term "hybrid gene" denotes a DNA sequence comprising on the one hand a DNA sequence encoding human EC-SOD as defined above and on the other hand a DNA sequence of the milk protein gene which is capable of mediating the expression of the hybrid gene product. The term "gene encoding a milk protein" or "milk protein gene" denotes an entire gene as well as an effective subsequence thereof capable of mediating and targeting the expression of the hybrid gene to the tissue of interest, i.e. the mammary gland. The milk protein gene may be the gene for β-lactoglobulin, α-lactalbumin or a casein, but the whey acid protein gene is particularly preferred. Normally, the effective subsequence is one which at least harbours one or more of a promoter region, a transcriptional start site, 3' and 5' non-coding regions and structural sequences. The DNA sequence encoding human EC-SOD is preferably substantially free from prokaryotic sequences, such as vector sequences, which may be associated with the DNA sequence after, e.g., cloning thereof.

The hybrid gene is preferably formed by inserting in vitro the DNA sequence encoding human EC-SOD into the milk protein gene by use of techniques known in the art. Alternatively, the DNA sequence encoding human EC-SOD can be inserted in vivo by homologous recombination.

Normally, the DNA sequence encoding human EC-SOD will be inserted in one of the first exons of the milk protein gene of choice or an effective subsequence thereof comprising the first exons and preferably a substantial part of the 5' flanking sequence which is believed to be of regulatory importance.

The hybrid gene preferably comprises a sequence encoding a signal peptide so as to enable the hybrid gene product to be secreted correctly into the mammary gland. The signal peptide will typically be the one normally found in the milk protein gene in question or one associated with the DNA sequence encoding human EC-SOD. However, also other signal sequences capable of mediating the secretion of the hybrid gene product to the mammary gland are relevant. Of course, the various elements of the hybrid gene should be fused in such a manner as to allow for correct expression and processing of the gene product. Thus, normally the DNA sequence encoding the signal peptide of choice should be precisely fused to the N-terminal part of the DNA sequence encoding human EC-SOD. In the hybrid gene, the DNA sequence encoding human EC-SOD will normally comprise its stop codon, but not its own message cleavance and polyadenylation site. Downstream of the DNA sequence encoding human EC-SOD, the mRNA processing sequences of the milk protein gene will normally be retained.

A number of factors are contemplated to be responsible for the actual expression level of a particular hybrid gene. The capability of the promoter as well of other regulatory sequences as mentioned above, the integration site of the expression system in the genome of the mammal, the integration site of the DNA sequence encoding human EC-SOD in the milk protein encoding gene, elements conferring post-transcriptional regulation and other similar factors may be of vital importance for the expression level obtained. On the basis of the knowledge of the various factors influencing the expression level of the hybrid gene, the person skilled in the art would know how to design an expression system useful for the present purpose.

The milk protein gene to be used may be derived from the same species as the one in which the expression system is to be inserted, or it may be derived from another species. In this connection it has been shown that the regulatory elements that target gene expression to the mammary gland are functional across species boundaries (which may be due to a possible common ancestor) [35].

Examples of suitable genes encoding a milk protein or effective subsequences thereof to be used in the construction of an expression system of the invention are normally found among whey proteins of various mammalian origins, e.g. a whey acidic protein (WAP) gene, preferably of murine origin, and a β-lactoglobulin gene, preferably of ovine origin. Also casein genes of various origins may be found to be suitable for the transgenic production of human EC-SOD, e.g. bovine aS1-casein and rabbit β-casein. The presently preferred gene is a murine WAP gene as this has been found to be capable of providing a high level expression of a number of foreign human proteins in milk of different transgenic animals [35].

Another sequence preferably associated with the expression system of the invention is a so-called expression stabilizing sequence capable of mediating high-level expression. Strong indications exist that such stabilizing sequences are found in the vicinity of and upstream of milk protein genes.

The DNA sequence encoding a human EC-SOD to be inserted in the expression system of the invention may be of cDNA, genomic or synthetic origin or any combination thereof. While some expression systems have been found to function best when cDNA encoding a desirable protein is used, others have been found to require the presence of introns and other regulatory regions in order to obtain a satisfactory expression [35]. In some cases it may be advantageous to introduce genomic structures in vector constructs compared to cDNA elements [56]. The intron and exon structure may result in higher steady state mRNA levels than obtained when cDNA based vectors are used.

In the specification, the term "intron" includes the whole of any natural intron or part thereof.

In a further aspect, the present invention relates to a hybrid gene comprising a DNA sequence encoding human EC-SOD inserted into a gene encoding a milk protein of a mammal, the DNA sequence being inserted in the milk protein gene in such a manner that it is expressible in the mammary gland of an adult female of a non-human mammal harboring the hybrid gene. The hybrid gene and its constituents have been discussed in detail above. The hybrid gene constitutes an important intermediate in the construction of an expression system of the invention as disclosed above.

In another aspect, the present invention relates to a non-human mammalian cell harboring an expression system as defined above. The mammalian cell is preferably an embryo cell or a pro-nucleus. The expression system is suitably inserted in the mammalian cell using a method as explained in the following.

In a further important aspect, the present invention relates to a method of producing a transgenic non-human mammal capable of expressing human EC-SOD, comprising injecting an expression system of the invention as defined above into a fertilized egg or a cell of an embryo of a mammal so as to incorporate the expression system into the germline of the mammal and developing the resulting injected fertilized egg or embryo into an adult female mammal.

The "non-human mammals" of the invention comprise all non-human mammals capable of producing a "transgenic non-human mammal" having a "desirable phenotype". Such mammals include rabbits, sheep, goats, murine species, bovine species, canine species, etc.

Desirable phenotypes for transgenic non-human mammals include, but are not limited to, the production of recombinant polypeptides in the milk of female transgenic non-human mammals.

The transgenic non-human mammals of the invention are produced by introducing a "transgene" into an embryonal target cell of the animal of choice. In one aspect of the invention, a transgene is a DNA sequence which is capable of producing a desirable phenotype when contained in the genome of cells of a transgenic non-human mammal. In specific embodiments, the transgene comprises a "recombinant DNA sequence" encoding a "recombinant polypeptide". In such cases, the transgene is capable of being expressed to produce the recombinant polypeptide.

The incorporation of the expression system into the germline of the mammal may be performed using any suitable technique, e.g. as described in [41] or in WO 91/08216.

Methods of introducing transgenes or overlapping transgene fragments into embryonal target cells include microinjection of the transgene into the pronuclei of fertilized oocytes or nuclei of ES cells of the non-human animal. Such methods for murine species are well known to those skilled in the art. Alternatively, the transgene may be introduced into an animal by infection of zygotes with a retrovirus containing the transgene [57]. The preferred method is microinjection of the fertilized oocyte. In this preferred embodiment, the fertilized oocytes are first microinjected by standard techniques. They are thereafter cultured in vitro until a "pre-implantation embryo" is obtained. Such pre-implantation embryos preferably contain approximately 16 to 150 cells. The 16 to 32 cell stage of an embryo is commonly referred to as a morula. Those pre-implantation embryos containing more than 32 cells are commonly referred to as blastocysts. They are generally characterized as demonstrating the development of a blastocoel cavity typically at the 64 cell stage. Methods for culturing fertilized oocytes to the pre-implantation stage include those described by Gordon et al. [58]; Hogan et al. [41] (for the mouse embryo); and Hammer et al. [59] (for rabbit and porcine embryos); Gandolfi et al. [60]; Rexroad et al. [61] (for ovine embryos); and Eyestone et al. [62]; Camous et al. [63]; and Heyman et al. [64] (for bovine embryos). Such pre-implantation embryos are thereafter transferred to an appropriate female by standard methods to permit the birth of a transgenic or chimeric animal depending upon the stage of development when the transgene is introduced. As is well known, mosaic animals can be bred to form true germline transgenic animals.

Since the frequency of transgene incorporation is often low, the detection of transgene integration in the pre-implantation embryo is highly desirable. In one aspect of the invention, methods are provided for identifying embryos wherein transgenesis has occurred and which permit implantation of transgenic embryos to form transgenic animals. In this method, one or more cells are removed from the pre-implantation embryo. When equal division is used, the embryo is preferably not cultivated past the morula stage (32 cells). Division of the pre-implantation embryo (reviewed by Williams et al. [65]) results in two "hemi-embryos" (hemi-morula or hemi-blastocyst) one of which is capable of subsequent development after implantation into the appropriate female to develop in utero to term. Although equal division of the pre-implantation embryo is preferred, it is to be understood that such an embryo may be unequally divided either intentionally or unintentionally into two hemi-embryos which are not necessarily of equal cell number. Essentially, all that is required is that one of the embryos which is not analyzed as hereinafter described be of sufficient cell number to develop to full term in utero. In a specific embodiment, the hemi-embryo which is not analyzed as described herein, if shown to be transgenic, is used to generate a clonal population of transgenic non-human animals.

One of each of the hemi-embryos formed by division of pre-implantation embryos is analyzed to determine if the transgene has been integrated into the genome of the organism. Each of the other hemi-embryos is maintained for subsequent implantation into a recipient female of the species.

The early identification of the pre-implantation embryos containing the integrated transgene is achieved by analyzing the DNA from one of each of the hemi-embryos. Such DNA is typically obtained by lysing the hemi-embryo and analyzing the thus released DNA. A polymerase chain reaction is performed to amplify all or part of the transgene. When the entire transgene is amplified, two extension primers each complementary to opposite strands at opposing ends of the transgene are used for amplification. Generally, the amplified DNA from the hemi-embryo is subjected to electrophoresis followed by hybridization with labeled probe complementary to the region of the transgene between the two extension primers. This facilitates the determination of the size of the amplified DNA sequences, if any, and provides an indication of whether the transgene has been integrated into the pre-implantation embryo from which the hemi-embryo was obtained (now called a "transgenic hemi-embryo"). If it has, the remaining untreated transgenic hemi-embryo is transplanted into a recipient parent. After in utero development, the transgenic non-human animal having the desired phenotype conferred by the integrated transgene is identified by an appropriate method in utero or after birth.

The above described methods for the detection of transgenesis in pre-implantation embryos provide economical and time saving methods for generating transgenic non-human animals since they significantly decrease the number of pregnancies required to produce a transgenic animal and substantially increase the likelihood that an implanted embryo will produce a transgenic non-human animal. Such methods are especially important for those animals for which very low or non-existent frequencies of transgenesis have been obtained, e.g. bovine species.

In an alternate embodiment, the above described method for detecting transgenesis in pre-implantation embryos is combined with embryonic cloning steps to generate a clonal population of transgenic embryos which may thereafter be implanted into recipient females to produce a clonal population of transgenic non-human animals also having the same genotype. In this regard, it is to be understood that transgenic embryos and/or non-human transgenic animals having the same "genotype" means that the genomic DNA is substantially identical between the individuals of the embryo and/or transgenic animal population. It is to be understood, however, that during mitosis various somatic mutations may occur which may produce variations in the genotype of one or more cells and/or animals. Thus, a population having the same genotype may demonstrate individual or subpopulation variations.

After a hemi-embryo is identified as a transgenic hemi-embryo, it is cloned. Such embryo cloning may be performed by several different approaches. In one cloning method, the transgenic hemi-embryo is cultured in the same or in a similar medium as used to culture individual oocytes to the pre-implantation stage. The "transgenic embryo" so formed (preferably a transgenic morula) is then divided into "transgenic hemi-embryos" which can then be implanted into a recipient female to form a clonal population of two transgenic non-human animals. Alternatively, the two transgenic hemi-embryos obtained may be again cultivated to the pre-implantation stage, divided, and recultivated to the transgenic embryo stage. This procedure is repeated until the desired number of clonal transgenic embryos having the same genotype are obtained. Such transgenic embryos may then be implanted into recipient females to produce a clonal population of transgenic non-human animals.

In a preferred cloning method, the transgenic embryo is cloned by nuclear transfer according to the techniques of Prather et al. [66]; Roble et al. [67]. According to this method, nuclei of the transgenic embryo are transplanted into enucleated oocytes, each of which is thereafter cultured to the blastocyst stage. At this point, the transgenic embryos may be resubjected to another round of cloning by nuclear transplantation or may be transferred to a recipient parent for production of transgenic offspring having the same genotype.

In addition to the foregoing methods for detecting early transgenesis, other methods may be used to detect transgenesis. Such method include in utero and post partum analysis of tissue. in utero analysis is performed by several techniques. In one, transvaginal puncture of the amniotic cavity is performed under echoscopic guidance [68, 69]. This involves recovering about 15 to 20 milliliters of amniotic fluid between about day 35 and day 100 of gestation. This volume of amniotic fluid contains about 1000 to 12,000 cells per ml originating from the urogenital tract, the skin and possibly the lungs of the developing embryo. Most of these cells are dead. Such cells, however, contain genomic DNA which is subjected to PCR analysis for the transgene as an indication of a successful transgenesis. Alternatively, fetal cells may be recovered by chorion puncture. This method may also be performed transvaginally and under echoscopic guidance. In this method, a needle is used to puncture the recipient animal's placenta, particularly the placentonal structures, which are fixed against the vaginal wall. Such sampling may be performed around day 60 of gestation in bovine species. Chorion cells, if necessary, are separated from maternal tissue and subjected to PCR analysis for the transgene as an indication of successful transgenesis.

Transgenesis may also be detected after birth. In such cases, transgene integration can be detected by taking an appropriate tissue biopsy such as from the ear or tail of the putative transgenic animal. About one to two centimeters of tail or about five to ten square millimeters of ear are obtained followed by southern blotting with a probe for the transgene according to the method of [42].

Normally, not all of the injected eggs will develop into transgenic mammals capable of expressing human EC-SOD. Transgenic founder animals can be identified e.g. as described in Example 2. About half of the mammals will from a statistically point of view be males. One the basis of the identified transgenic individuals—male and female—progeny can be established and stable lines of transgenic animals established.

Once integrated in the germ line, the DNA sequence encoding human EC-SOD may be expressed at high levels to produce a correctly processed and functional human EC-SOD. Transgenic females from which recombinant polypeptide can be harvested can thus be bred in the following generations.

In a further aspect, the present invention relates to a transgenic non-human mammal prepared by a method as described above.

The DNA used to make transgenic cells and animals preferably comprises genomic DNA rather than cDNA. This is because the expression of transgenes is preferably limited to tissue-specific expression as well as temporal-specific expression. When the transgene is derived from genomic DNA, important cis-acting regulatory sequences such as enhancers and other regulatory elements, located either in introns or in regions distant from the structural gene, can be included. Such regulatory sequences are lost during transcription and RNA processing and accordingly are not generally available with cDNA-derived transgenes.

In a further aspect, the present invention relates to a transgenic non-human mammal prepared by a method as described above.

While the transgenic non-human mammal of the invention in its broadest aspect is not restricted to any particular type of mammal, the mammal will normally be selected from the group consisting of rabbits, mice, rats, sheep, pigs, goats, lamas, camels and cattle. For large scale production of human EC-SOD the larger animals such as sheep, goats, pigs and especially cattle are normally preferred due to their high milk production. However, also mice, rabbits and rats may be interesting due to the fact that the manipulation of these animals is more simple and results in transgenic animals more quickly than when, e.g. cattle, are concerned.

Also progeny of a transgenic mammal as defined above, capable of producing human EC-SOD is within the scope of the present invention.

From the above explanation it will be clear that the present invention for the first time makes it possible to produce milk from a non-human mammal comprising human EC-SOD, the importance and utility of which will be apparent from the present context. Thus, in a further aspects of the present invention includes milk from a non-human mammal comprising recombinant human EC-SOD. Of particular interest is milk from a non-human mammal comprising a polypeptide of the invention as defined above comprising the amino acid sequence shown in SEQ ID NO:2 or a polypeptide encoded by a DNA sequence or a variant or subsequence thereof as defined above. Typically, the milk of the invention will be obtained from a transgenic mammal of the invention as defined above.

In another aspect, the present invention relates to a method of obtaining human EC-SOD comprising collecting milk from a transgenic non-human mammal of the invention as defined above and recovering the human EC-SOD from the milk. The milk may be collected in any suitable manner normally used in connection with the collection of milk from the mammal in question.

The polypeptide of the invention having the superoxide dismutating property of native EC-SOD may be used for the diagnosis, prophylaxis or treatment of diseases or disorders connected with the presence or formation of superoxide radicals and other toxic oxygen intermediates derived from the superoxide radical.

Examples of such diseases or disorders are selected from conditions involving ischaemia followed by reperfusion, e.g. infarctions such as heart, kidney, brain, spinal cord, or intestinal infarctions; transplantation of organs such as heart, lung, pancreas, liver, skin, bone tissue, severed extremities, skeletal muscle; inflammatory diseases such as rheumatoid arthritis, pancreatitis, in particular acute pancreatitis, pyelonephritis and other types of nephritis, and hepatitis, neuritis, uveitis, cystitis, peyronies disease, autoimmune diseases, insulin-dependent diabetes mellitus, disseminated intravascular coagulation, fatty embolism, haemorrhagic shock, endotoxin-induced shock, septicemia, severe viral infections, adult respiratory distress, infantile respiratory distress, brain haemorrhages in neonates, burns, preservation of lens and cornea in the context of transplantation, adverse effects of ionizing radiation, carcinogenesis, and adverse effects of toxins such as alloxan, paraquat, and some cytostatic compounds.

Thus, the polypeptide of the invention is indicated for substantially the same applications as CuZn SOD the therapeutic activity of which has been more thoroughly documented as discussed below. EC-SOD and the EC-SOD variants of the invention have, however, been found to possess a number of characteristics which are assumed to make them particularly useful for therapeutic applications. CuZn SOD has a low molecular weight (33,000) which causes it to become eliminated very quickly by glomerular filtration in the kidneys so that in rodents it has a plasma half-life of less than 10 minutes and, in human beings, the enzyme has a half-life of about 20–30 minutes. EC-SOD C [15] and the EC-SOD variants have a much longer half-life. This is partly due to the high molecular weight of EC-SOD which prevents it from being eliminated by glomerular filtration, and partly due to the fact that EC-SOD and EC-SOD variants having heparin affinity of the C-type seem to bind to endothelial cell surfaces. In the therapeutic use of EC-SOD and variants according to the invention, the enzyme therefore preferably has a half-life in human beings of at least 4 hours and possibly even longer.

As explained above, EC-SOD is, in its native environment, a secreted protein and it is therefore likely that it is specifically synthesized for a function in extracellular space (in extracellular fluids or on cell surfaces) which may cause it to exhibit properties which are particularly well adapted to protect plasma components or the outer surface of cells against the toxic effects of superoxide radicals or other oxygen radicals. A fundamental property of EC-SOD C, and most likely also a polypeptide having a slightly reduced affinity for heparin compared to the heparin affinity of recombinant EC-SOD C, e.g. the variant T216, is its affinity for heparan sulfate which in vivo apparently has the correlate of binding to heparan sulfate proteoglycan in the glycocalyx of cell surfaces and in the interstitial connective tissue matrix. This property would seem to be a particularly efficient way to protect cells and tissues against an external superoxide radical source.

The significance of the apparent association of EC-SOD and EC-SOD variants with cell membranes is further supported by the finding that CuZn SOD which has been modified with polylysine to bind to cell membranes is better able to protect activated (superoxide radical-producing) polymorphonuclear leukocytes (PMN) from autoinactivation (cell death) than normal CuZn SOD which is negatively charged and therefore tends to be repelled by the cell membranes. The fact that Nocardia asteroides possesses a membrane-associated SOD which appears to confer efficient protection against activated human PMNs as the susceptibility of Nocardia to PMNs is significantly increased when Nocardia cells are treated with antibodies towards this SOD also points to a cell membrane-protective function of SOD bound to cell surfaces. Unlike EC-SOD and EC-SOD variants, CuZn SOD has an intracellular function which may make it less well suited for extracellular application, i.e. occasioned by the extracellular presence of superoxide radicals. Furthermore, its brief half-life compared to that of EC-SOD and EC-SOD variants mentioned above would seem to make it necessary to administer larger doses at shorter intervals than is likely to be the case with the EC-SOD variants of the invention.

Parenterally administered CuZn SOD has been shown to exhibit an anti-inflammatory effect in a series of animal models of inflammation as well as in inflammatory diseases in animals. In humans, positive effects of CuZn SOD have been reported in rheumatoid arthritis and arthroses, in inflammation of the bladder and other urological conditions.

Parenterally administered CuZn SOD is not taken up by the cells and must exert its activity in the extracellular space. CuZn SOD encapsulated in liposomes is taken up by the cells and is reported to be effective against Crohn's disease, Bechet's disease, dermatitis herpetiformis, ulcerative colitis, Kawasaki's disease and against the adverse effects of radiation therapy. The mechanism of the anti-inflammatory activity of CuZn SOD is not quite clear. Direct protection against oxygen radicals formed by activated leukocytes has been suggested. Another possibility is prevention of the formation of a superoxide induced strongly chemotaxic substance.

The other large potential area of application for SOD is as a protective factor against tissue damage caused by ischaemia followed by reperfusion. If the supply of blood to a tissue is cut off, the tissue will slowly become necrotic. Macro- and microscopically the damage will typically develop slowly over many hours. If the tissue is reperfused after, for instance, one hour, a strong acceleration of the tissue damage will occur instead of an improvement. Most likely there are several reasons for this so-called reperfusion paradox, but oxygen radicals formed as a result of the re-appearance of oxygen in previously ischaemic tissue appear to contribute to the damage. The radicals are extremely short-lived and therefore difficult to study directly, and much of the information concerning their formation and effects is inferred from the protective action of various oxygen radical scavengers. Their formation have however also been demonstrated more directly by means of EPR on heart samples. Tissue protection by means of CuZn SOD has been demonstrated in ischaemia- or anoxia-reperfusion models in the kidney.

It is contemplated that EC-SOD and EC-SOD variants might be used in connection with thrombolytic agents such as streptokinase, tissue plasminogen activator, urokinase and variants and variants of these factors.

The source of oxygen radicals in this situation is not completely clear, but the effect of allopurinol seems to indicate that it is partly caused by xanthine oxidase which, by ischaemia, is converted from its xanthine dehydrogenase form to the radical-producing oxidase form. A large amount of hypoxanthine which is the substrate for xanthine oxidase is formed due to purine nucleotide degradation induced by ischaemia. Other sources of superoxide radicals may be activated leukocytes attracted to ischaemia-damaged tissue, prostaglandin synthesis, $O_2.^-$ is a byproduct; and autooxidation of various compounds accumulated in reduced form during ischaemia. The finding concerning ischaemia followed by reperfusion has potentially important clinical applications.

It may be possible to obtain an excellent effect by reperfusion of tissue in connection with heart infarctions, by the concomitant administration of a SOD such as EC-SOD or a polypeptide of the invention and/or other protective factors against oxygen radicals and thrombolytic factors, e.g. tissue plasminogen activator. The results of the SOD experiments also indicate a possible application in connection with heart surgery and heart transplantations. Analogously, the results of employing an SOD in connection with kidney ischaemia followed by reperfusion indicate that SOD may be employed in connection with kidney transplantations and other organs transplantations such as skin, lung, liver, pancreas, bone tissue transplantations. Ischaemic brain disease is another possible indication.

In the case of, for instance, burns, immunocomplex formation, and major tissue damage, neutrophilic leukocytes are accumulated in the lungs. Complement activation (C5 a) often seems to mediate the accumulation. The leukocytes seem to be activated and release oxygen radicals, thereby causing lung damage which, for instance, is characterized by increased vessel permeability and lung oedema (adult respiratory distress). In several animal models, SOD and other oxygen radical scavengers have been shown to have a protective effect against lung damage.

Concerning the central nervous system protective effects of CuZn SOD have been shown against posttraumatic brain oedema.

The endothelium-derived vessel relaxant factor (EDRF) is very sensitive to superoxide, and administration of SOD augments its actions. Superoxide radical production can occur under many circumstances in the body and may cause vasoconstriction and decreased tissue perfusion. Administration of SOD is believed to be able to relieve such vasoconstriction and also to enhance other effects of EDRF such as platelet stabilization.

Acute severe increase in blood pressure leads to functional and morphologic abnormalities in brain arterioles. Prostaglandin synthesis inhibitors and superoxide dismutase is contemplated to protect against the abnormalities. Superoxide release can be detected. Close analysis of the model has led to the conclusion that superoxide radicals are formed as a byproduct during prostaglandin synthesis. The results suggest that tissue damage caused by superoxide radicals released during prostaglandin synthesis may occur in other pathological situations and that SOD may exert a protective action.

In various types of autoimmune disease, such as systemic lupus erythematosus (SLE), systemic sclerosis and rheumatoid arthritis, an increased frequency of chromosomal breaks in lymphocytes has been demonstrated.

The neoplastic transformation of cells is usually divided into two phases, i.e. initiation followed by promotion. In in vitro models where initiation has been caused by ionizing radiation, bleomycin, misonidazole and other nitroimidazoles, the oncogenic transformation has been effectively inhibited by the presence of SOD in the medium. It is not necessary for SOD to be present during exposure to the initiating substances which seems to indicate that the enzyme inhibits the subsequent promotion step. Non-toxic doses of xanthine+xanthine oxidase cause promotion in growing cells. Addition of SOD or SOD+catalase inhibits this effect. Phorbol esters are known promoters. In a model in which skin tumors were induced by initiation with a benzanthracene followed by application of a phorbol ester (TPA), local treatment with a lipophilic copper complex with SOD activity strongly reduced tumor formation. The result indicates that, at least in certain cases, superoxide radicals contribute to the promotion of tumor formation and that SOD may protect against this effect.

There is reason to believe that oxygen radicals contribute to the damaging effects of a number of toxic substances such as bleomycin, adriamycin, alloxan, 6-hydroxydopamine, paraquat, dihydroxyfumaric acid, nitrofurantoin and streptozotocin. In those cases where radical formation takes place in the extra-cellular space it might be possible to protect by means of injected protective enzyme. Thus, SOD may protect against the diabetogenic activity of alloxan (damages β-cells in the pancreas) in vitro and in vivo. The damaging effect of alloxan seems therefore to be mediated by the superoxide radical or by other oxygen radicals derived from it. In diabetes mellitus there is an infiltration in the Langerhans' islets by inflammatory cells which potentially may form oxygen radicals. It may therefore be contemplated to protect the β-cells by injections with SODs such as EC-SOD or a polypeptide of the invention at the first onset of diabetes mellitus.

Recombinant EC-SOD C has been found to be more efficient than CuZn SOD in disease models in which the two SODs have been tested in parallel. Thus, recombinant EC-SOD C has been shown to reduce the concentration of oxygen-free radicals in reperfused rat hearts. The effect of rEC-SOD C in reducing the free radical concentrations was concluded to be at least of the same extent as CuZn SOD. Furthermore, recombinant human EC-SOD C has been shown to reduce myocardial damage in rats subjected to ischemia and 24 hours of reperfusion.

The dosage and timing of polypeptide of the invention injections depend on the half-life of the enzyme in human blood vessels. It may as in rabbits be about 15 hours. The half-life in humans is however probably longer. Assuming first-order kinetics and a half-life of 36 hours, daily injections of 35 mg after an initial injection of 87 mg would therefore result in the same concentration as after the initial injection.

The therapeutic usefulness of the polypeptides of the invention may vary according to the particular disease to be treated. When strong binding to cell-surfaces is advantageous EC-SOD C or the polypeptides of the invention with even stronger heparin affinity may be most useful, for example in transplantation of organs or if a polypeptide of the invention is to be injected into an inflamed organ.

In yet other conditions a more limited heparin affinity such as that of a polypeptide having a slightly reduced affinity e.g the polypeptide. T216, described herein, may be advantageous. In a situation in which the time of reperfusion cannot be predicted precisely (e.g. thrombolysis of coronary artery or artery in other organs) a strong binder such as EC-SOD C injected before reperfusion would bind firmly to endothelium around the body and very little would be available to protect immediately the reperfused organ territory at reperfusion. A polypeptide having a slightly reduced affinity, e.g the polypeptide T216 described herein, would in this situation exist in relatively high concentration in the plasma phase, but would still bind endothelium and is also likely to redistribute more rapidly between binding sites in organs. Only EC-SOD variants with a heparin affinity of a magnitude which results in elution from a Heparin-Sepharose® column at a NaCl concentration of 0.55M or higher (under the conditions stated in Example 6) will bind to endothelium in vivo. Such variants may be advantageous in conditions where some but variable degree of cell-surface binding is valuable.

Variants which apparently do not bind heparan sulfate in vivo, A and B-types, may finally be useful when a high SOD activity in plasma or the interstitial fluid phase is important.

For topical treatment, far less of a polypeptide composition of the invention as described above would probably be needed. At present, 4–8 mg of CuZn SOD are administered intraarticularly once a week for the treatment of arthritis. EC-SOD which has a far higher molecular weight is likely to remain in the joint for a longer period of time. A similar treatment protocol or possibly somewhat lower doses will probably be appropriate.

The polypeptide of the invention having the superoxide dismutating property of native EC-SOD may further be used in cosmetics, e.g. to prevent skin ageing and protect against radiation damages. The polypeptide may be in a liposome composition.

LEGEND TO FIGURES

FIG. 1 C-terminal cDNA sequences and amino acid sequences of native EC-SOD and 12 EC-SOD variants.

FIG. 2 Structure of the recombinant WAP/BC-SOD gene and identification of hEC-SOD Transgenic Mice by Southern Analysis.

A. Structure of the WAP/EC-SOD transgene. To direct expression of recombinant human EC-SOD to the mammary gland of transgenic mice a hybrid WAP/EC-SOD gene, pS172, was constructed. This recombinant gene comprises about 2.3 kb of upstream regulatory sequences including the first 24 bp of the transcribed but untranslated WAP sequence in front of the human EC-SOD cDNA. Downstream of the cDNA, a WAP genomic fragment of about 4 kb extending from the SAlI site located in the third exon to the EcoRI site located about 1.6 kb 3' of the last exon was inserted.

B. Southern blot analysis of integrated WAP/EC-SOD transgenes. Tail DNA, 10 μg, from each animal was restricted with samHI, electrophoresed on 1% agarose gel, transferred to membranes and hybridized to a 32P-labelled probe of EC-SOD cDNA. The hybridizing band of 1.8 kb contains the EC-SOD cDNA and 3' WAP sequences. Lane 1 is a control whereas lanes 2–15 each represent an animal.

FIG. 3 Tissue distribution of WAP/EC-SOD mRNA expression in a lactating female of line #68, 11 days after parturition.

A) 10 μg of total RNA from various tissues was electrophoresed on agarose-formaldehyde gel, transferred to Gene Screen Plus membranes (New England Nuclear) and hybridized with a 32P-labelled EC-SOD cDNA probe. The RNA hybridization results show expression in the lactating mammary gland of a 1 kb major EC-SOD mRNA species; no hybridization to RNA prepared from non-transgenic animals was observed.

The tissues were mammary gland (Mg), liver (Li), kidney (Ki), spleen (Sp), heart (He), lung (Lu), salivary gland (Sg) and brain (Br). RNA sizes in kb, determined by co-electrophoresis of a RNA ladder (BRL) is indicated to the left.

B) Northern blots of mammary gland RNA of transgenic line #68 and controls were hybridized with a mouse WAP exon 3 and exon 4 probe, which hybridizes to the same extend to both endogenous WAP MRNA and to recombinant WAP/EC-SOD MRNA. The endogenous WAP MRNA level was found to be significantly higher than the level of recombinant WAP/EC-SOD MRNA. The β-lactoglobulin/EC-SOD transgenic lines were not analysed for mRNA expression.

Figure 4:
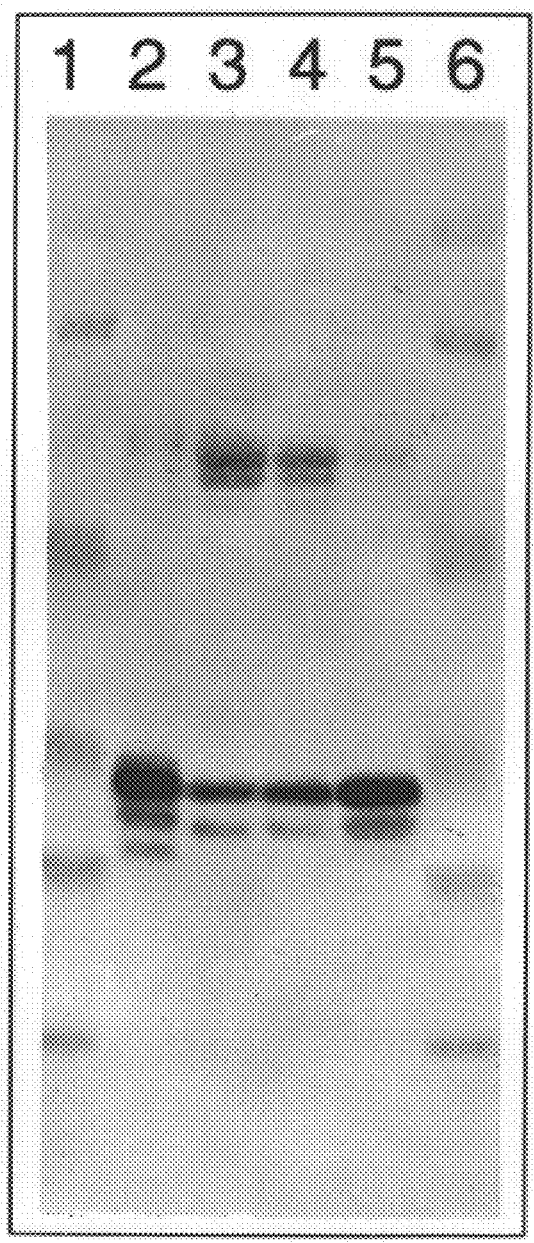

FIG. 4 Tmmunoblot of human EC-SOD produced in milk from a transgenic mouse of line #68. Electrophoresis, transfer and development was performed as described in materials and methods. Approximately 400 ng of EC-SOD was applied to each lane. Lanes 1 and 6: Molecular weight markers (116.5, 80, 49.5, 32.5, 27.5 and 18.5 kDa). Lane 2: Recombinant EC-SOD produced in CHO cells. Lanes 3–5: The whey fraction of milk collected at day 4, 10 and 18 post parturition, respectively.

Figure 5:
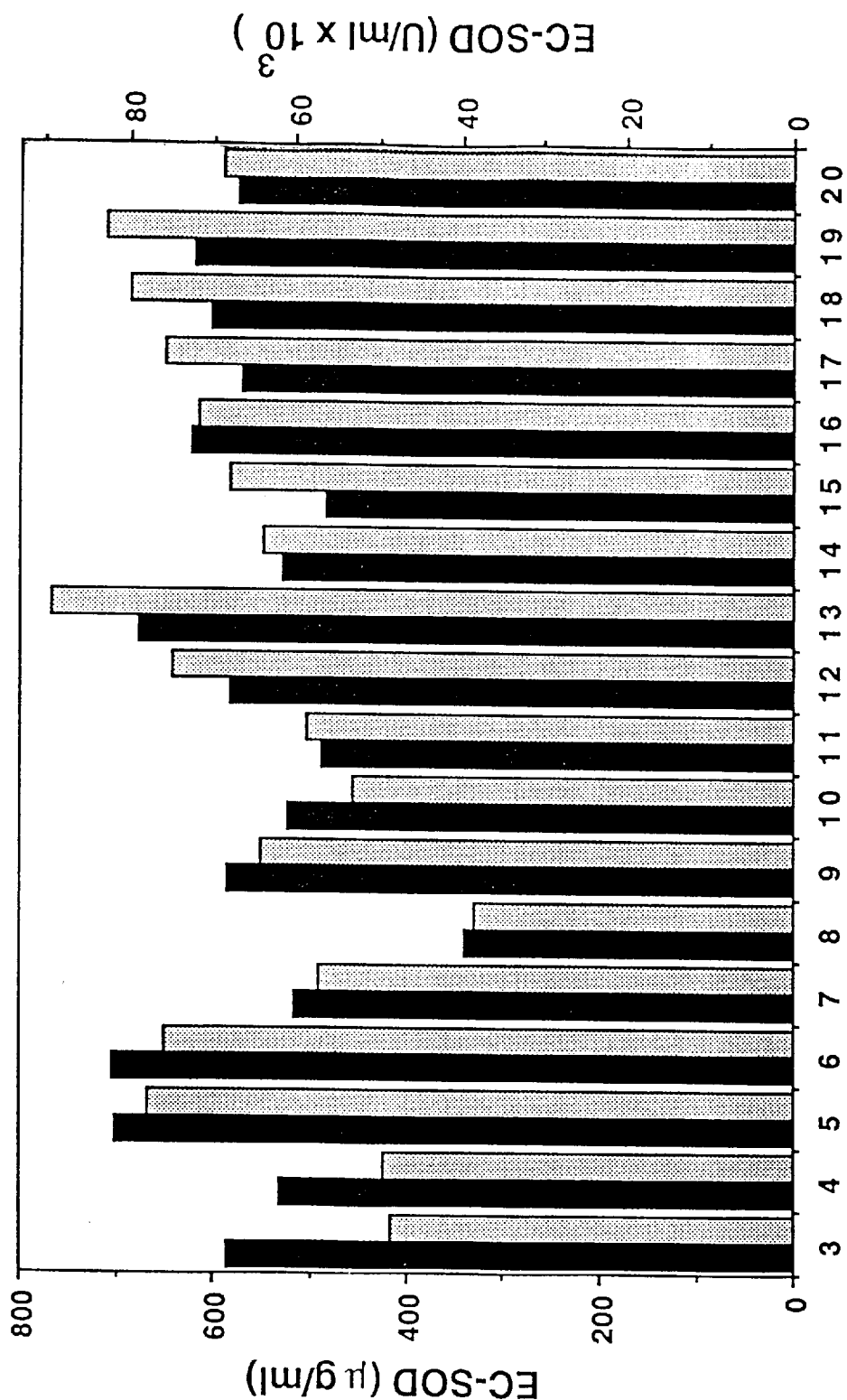

FIG. 5 The EC-SOD production in milk from a transgenic mouse of line #68 was followed over lactation. Recombinant EC-SOD levels were determined both with ELISA and SOD activity analysis. The scales for these parameters were chosen so that EC-SOD with specific activity identical to that of native and CHO produced recombinant human EC-SOD (8.6 ng/U, ref. 13) will form columns for amount of protein and enzymatic activity of equal heights, the columns in black show ELISA concentration and the dotted columns show activity. Milk samples were withdrawn daily as indicated.

Figure 6:
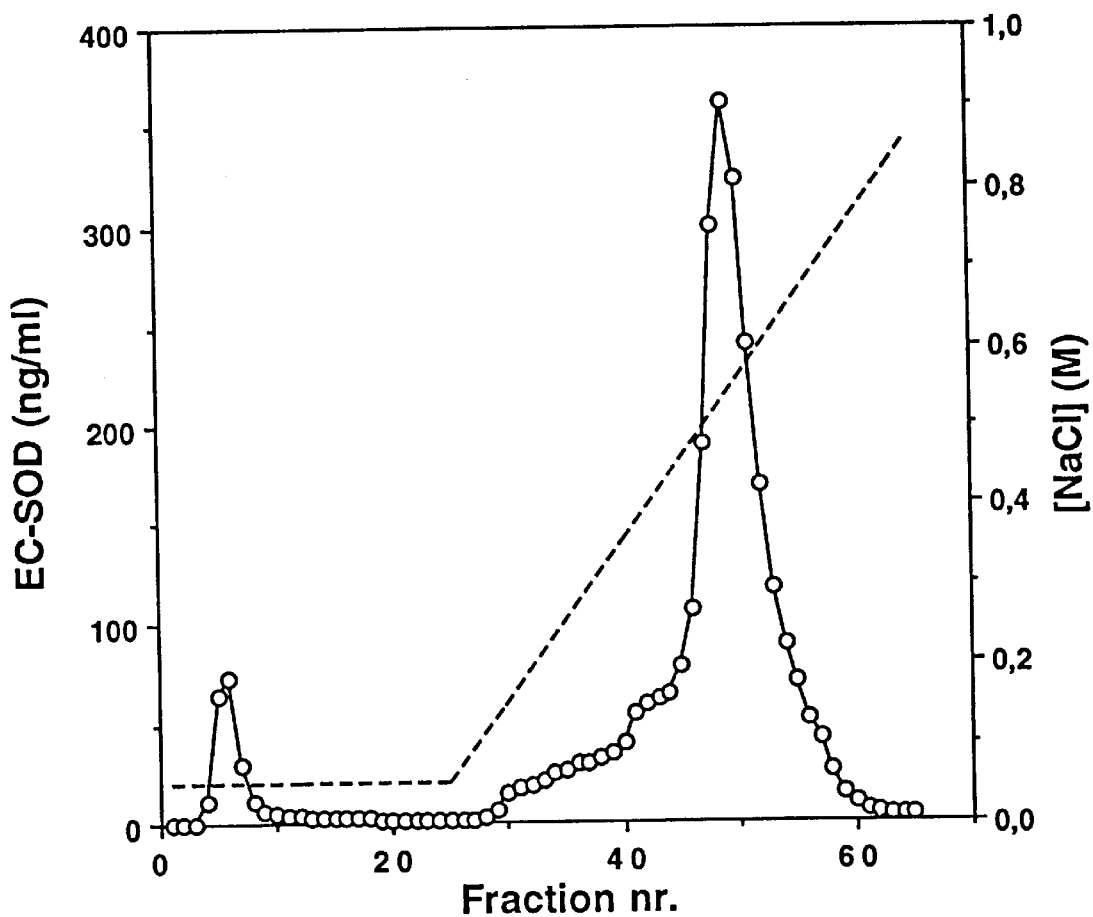

FIG. 6 Analytical separation of milk derived recombinant EC-SOD on Heparin-Sepharose. Milk from line #68, containing about 1800 ng EC-SOD was applied to and separated on a Heparin-Sepharose column as described in the Materials and Methods section (—o—o—), (————) the gradient in NaCl.

Figure 7:
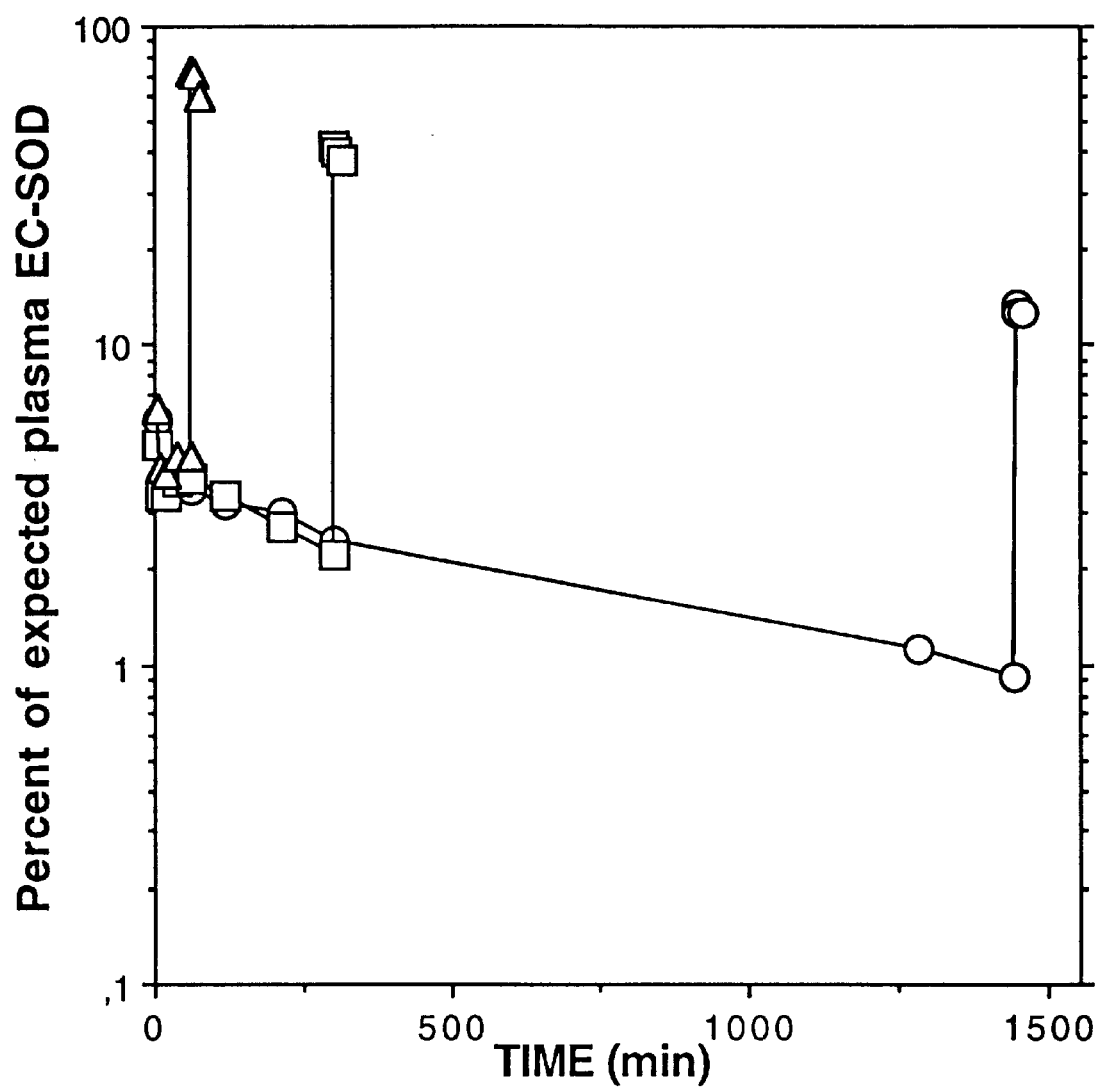

FIG. 7 Plasma clearance of recombinant human EC-SOD from mouse milk in rabbits. The figure shows the time-course in plasma of EC-SOD produced in milk of transgenic mice injected intravenously into rabbits, as described in Materials and Methods. The expected plasma concentration was calculated from the amount injected and the plasma volume as determined with $^{125}$I-albumin. The experiments were terminated after 1 (△), 5 (■) or 24 (o) by intravenous injection of a large dose heparin followed by collection of blood sample after 2, 5 and 15 min.

EXAMPLES

The following examples are intended to illustrate but not to limit the present invention.

Construction of the expression systems of the invention, and the molecular biological characterization of it, employs standard methods generally known in the art of recombinant DNA. Unless otherwise stated, the methods used are those described by Sambrook et al., 1989 [70] and Ausubel et al., 1991 [71].

DEFINITIONS

Hybridization of DNA

DNA, e.g. present on nitrocellulose filters, are wetted in 2× SSC [1× SSC: 0.15M NaCl, 0.0015M Na$_3$-citrate, pH 7.0] and placed in a heat-sealed plastic bag with pre-warmed (67° C.) prehybridization solution. Prehybridization takes place for 2 h at 67° C., the bag being gently shaken. The solution is exchanged with pre-warmed (67° C.) hybridization solution, a radioactive probe is added and hybridization is carried out at 67° C. for 18 h. The bag is gently shaken to ensure constant movement of the liquid over the nitrocellulose filters. After hybridization, a washing procedure is carried out.

The radioactive probe is prepared by use of known methods, e.g. as described by Sambrook et al. [70], on the basis of the DNA sequence shown in SEQ ID NO:1 or a part thereof, especially a coding part such as the nucleotides corresponding to amino acids 1–210 or an effective subsequence of the DNA sequence as defined above.

The prehybridization and hybridization solutions used are: 10× Denhardt's, 4× SSC, 0.1% SDS, 10 μg/ml polyA, 50 μg/ml of denatured DNA to be analyzed and the denatured (heat) radioactive probe. The filters are washed in pre-warmed (67° C.) solutions: 10× Denhardt, 2× SSC, 0.1% SDS for 2×15 min. and 1× SSC, 0.1% SDS for 4×15 min. The filters are air-dried and covered with Vita-Wrap, and X-ray film is exposed to the filters for 3 h to 3 weeks with and without intensifying screens.

Example 1

Construction of transgenes 3 vectors were constructed, pS172, pS315 and pS387.

The human EC-SOD cDNA[12] was subcloned as a 1396 bp EcoRI fragment into pUC18. The cDNA was modified in the 5'end by insertion of a HindIII linker 32 bp upstream of the start codon and at the 3'end by insertion of a SalI linker downstream of the translational stop. To facilitate introduction of human EC-SOD cDNA under control of the WAP promoter, a plasmid harbouring the 7.2 kb EcoRI fragment containing the murine WAP gene [39] was digested with KpnI and a HindIII linker was inserted. The resulting plasmid was digested with HindIII and SalI thereby removing the sequence between KpnI in exon I and SalI located in exon III of the WAP gene. This fragment was then ligated with the HindIII/SalI human EC-SOD cDNA fragment. The resulting vector, pS172, was then digested with EcoRI and a fragment of about 5.9 kb (FIG. 2) was isolated and purified by electro-elution before injection into mouse embryos.

A variant of pS172 was also generated. This vector, pS315, has a longer 5'WAP of about 4.5 kb and the translational start of EC-SOD was inserted directly downstream of the KpnI site in exon I of the murine WAP gene. This KpnI site is located just upstream of the translational start of WAP. The WAP/EC-SOD recombinant gene was isolated, purified by electroelution and injected as described below.

A third variant of expression vector containing 1.8 kb ovine β-lactoglobulin upstream regulatory sequence [40] in front of human EC-SOD cDNA was constructed. The ovine β-lactoglobulin promoter fragment was cloned as a BamHI/PvuII fragment into BamHI/SmaI digested pUC19. From this plasmid, the promoter fragment was then isolated as a 1.8 kb HindIII/KpnI (partial digestion) fragment. This β-lactoglobulin promoter fragment was then ligated to a human EC-SOD cDNA which was modified by insertion of a KpnI site in front of the start codon. Downstream of the EC-SOD stop codon, a murine 4.6 kb WAP genomic fragment was inserted, providing the mRNA processing signals. This 4.6 kb WAP fragment extends from the KpnI site, which was changed to a SalI, in the first exon to the EcoRI site located about 1.6 kb downstream of the last exon. The β-lactoglobulin/ECSOD/WAP fragment was isolated from the resulting expression vector, pS387, and injected.

The milk protein gene sequences were kindly provided by Dr. Lothar Hennighausen.

Injection

An EcoRI fragment (FIG. 2) was isolated from the plasmid pS172 and used for injection. Alternatively, the WAP/ECSOD fragment of pS315 or β-lactoglobulin/EC-SOD/WAP fragment of pS387 was isolated and injected. The isolated fragments were injected into the pronucleus of C57B1/6JxCBA-f2 or C57B1/6JxDBA/2J -f2 embryos obtained after priming of donor female mice with 5 IU pregnant mare's serum gonadotropin followed by 5 IU human chorion gonadotropin 48 h later for superovulation of the mice. The C57B1/6JxCBA-f1 animals were obtained from Bomholtgaard Breeding and Research Centre Ltd. (Ry, Denmark). The injections were performed using Narishigi hydraulic micromanipulators and a Nikon inverted microscope [41]. After injection the embryos were implanted in pseudo-pregnant C57B1/6JxCBA-f1 recipients.

Results

To direct expression of recombinant human EC-SOD to the mammary gland of transgenic mice a hybrid WAP/EC-SOD gene, pS172, was constructed. This recombinant gene comprises about 2.3 kb of upstream regulatory sequences including the first 24 bp of the transcribed but untranslated WAP sequence in front of the human EC-SOD cDNA. Downstream of the cDNA, a WAP genomic fragment of about 4 kb extending from the SalI site located in the third exon to the EcoRI site located about 1.6 kb 3' of the last exon was inserted (FIG. 2A). To generate WAP/EC-SOD transgenic animals 178 injected ova at one-cell stage were implanted into 7 foster mothers resulting in 19 newborn mice. 14 animals were analyzed and five mice were identified as carrying WAP/EC-SOD sequences (founder animals) using PCR analysis, and the presence and the integrity of the injected DNA was confirmed with Southern blot analysis (FIG. 2B). Three of the founder animals were females and two were males. One female founder was lost. Founder animals were bred and lactating females were generated from all the lines.

The β-lactoglobulin/EC-SOD construct was injected in 160 ova which were implanted into 16 foster mothers. This resulted in birth of 28 mice which were analyzed. Among these, three mice were identified to be transgenic and were analyzed for expression of recombinant protein.

Conclusion

Five lines of transgenic mice with integrated WAP/EC-SOD gene were identified. Active recombinant EC-SOD was obtained in milk from such animals and expression of the recombinant gene was found predominantly in the mammary gland. The β-lactoglobulin/EC-SOD hybrid gene was integrated into three lines of transgenic mice. This construct was found to mediate very low levels of human ECSOD expression in the mammary gland. The level of active human EC-SOD in milk from β-lactoglobulin/-EC-SOD transgenic mice was below 10 ng/ml whereas the WAP/-EC-SOD hybrid gene mediated levels up to 0.7 mg/ml. No correlation between expression levels and copy number of the recombinant EC-SOD genes could be observed. This is in agreement with other studies [48, 49].

Example 2

Early identification of transgenes

Mice having integrated the transgene were identified with PCR analysis of DNA from tail biopsy specimens obtained three weeks after birth of the animals. Biopsies were incubated in 0.6 ml urea lysis buffer containing; 1M Urea, 50 mM Tris-HCl pH 8.0, 0.1M NaCl, 0.5% SDS, 5 mM EDTA and 200 mg/ml proteinase K. Samples were incubated overnight at 37° C. PCR analysis was performed in 50 mM KCl, 10 mM Tris-HCl pH 8.4, 1.5 mM $MgCl_2$, 0.25 mM DNTP, 2.5 U Taq polymerase (BRL, Gaithersburg, Md.), using primers complementary to WAP (5'-CTGTGTGGCCAAGAAGGAAGTTTGT-3') (SEQ ID NO:3), β-lactoglobulin (5'GCCTGAGGATGAGCCAAGTG-3') (SEQ ID NO:4) and EC-SOD (5-GTCCAGCGTGGCCGACGGCTGCACCTG-3') (SEQ ID NO:5) sequences, respectively. Positive results were confirmed by Southern blot analysis using the human EC-SOD cDNA as a probe [42].

Example 3

Expression of transgenes

Expression of the transgenes were assessed by analyzing RNA and milk from lactating females that were either $f_0$ animals or the transgenic $f_1$ offspring of $f_0$ males.

RNA isolation and analysis

Total RNA from various tissues of transgenic lactating female mice was isolated [42]. Samples of 10 μg total RNA was fractionated on MOPS/formaldehyde agarose gels and transferred to Gene Screen plus membranes (New England Nuclear, Boston, Mass.), and subsequently hybridized to a $^{32}$P-labelled probe according to the supplier's protocol (Amersham, U.K.).

The RNA hybridization results show expression in the lactating mammary gland of a 1 kb major EC-SOD mRNA species (FIG. 3A). This in agreement with the expected mRNA size. No hybridization was observed to RNA prepared from non-transgenic animals.

The tissue distribution of recombinant WAP/EC-SOD expression was investigated in duplicate mice, of the transgenic lines. Analysis of RNA prepared from various tissues (FIG. 3A) showed that abundant expression of recombinant EC-SOD was restricted to the lactating mammary gland. However, low levels of recombinant EC-SOD expression was also detected in brain. In additional experiments, where the same WAP regulatory sequences were used to direct expression of other human cDNAs, no recombinant gene expression was detected in the brain.

Northern blots of mammary gland RNA of transgenic line #68 and controls were hybridized with a mouse WAP exon 4 probe, which hybridizes to both endogenous WAP MRNA and to recombinant WAP/EC-SOD MRNA. The endogenous WAP MRNA level was found to be significantly higher than the level of recombinant WAP/EC-SOD MRNA (data not shown). The βlactoglobulin/EC-SOD transgenic lines were not analyzed for MRNA expression.

Example 4

Milk collection

Mice were anaesthetized with 0.017 ml Avertin (2.5%) per g body weight [41] and given 0.2 IE oxytocin (Partocon, Ferring, Lund, Sweden) intraperitoneally ten minutes before milk collection. The milk was collected using a milk apparatus which collected the milk by continuous suction into chilled 1.5 ml Eppendorf tubes. After collection the milk was immediately frozen in −70° C.

Example 5

Determination of EC-SOD in mouse milk

Partial purification of EC-SOD produced in transgenic mice

Milk collected from mice were diluted ten times with distilled water and thereafter centrifuged at 8000× g for 5 min. The lipid layer at the surface was carefully removed and the supernatant was collected. The skimmed milk was diluted 1:1 with 50 mM sodium phosphate, 0.5M NaCl, pH 7.0 (buffer A) and thereafter applied to a column with a monoclonal antibody directed against native human EC-SOD coupled thereto. The column was washed with buffer A and eluted with 50 mM AMP-HCl, 1M KSCN, pH 9.0. The eluate was ultrafiltrated and transferred to distilled water and stored frozen at −20° C. The protein concentration of collected fractions was measured using the method of Bradford [43].

Enzyme-linked immunosorbent assay (ELISA) for human EC-SOD

Quantitation of human EC-SOD was made using the double antibody sandwich ELISA method. Microtiter plates (Nunclon; Nunc, Roskilde, Denmark) were coated with 100 μl per well of a solution containing 16 μg/ml of polyclonal rabbit anti-EC-SOD IgG antibodies in 50 mM $Na_2CO_3$, pH 9.6. After 2 h incubation at room temperature, the wells were washed with blocking buffer (10 mM Na phosphate, pH 7.4, 140 mM NaCl, 0.1 % wt/vol Tween 20, and 0.5% BSA) and then blocked overnight with 300 μl blocking buffer. For analysis, 50-μl samples, diluted if necessary with blocking buffer, were added to each well and incubated for 2 h. The wells were then washed with blocking buffer, and 50 μl 3 μg/ml monoclonal anti-EC-SOD antibody B6,H6 which is described in, and produced according to, Example 15 of WO 87/01387 and 50 μl peroxidase-conjugated rabbit anti-mouse IgG (DAKOPATTS, Copenhagen, Denmark), both dissolved in blocking buffer, added in that order. After a further 2 h, the wells were washed with blocking buffer and then developed for 10 min with 100 μl 3.7 mM O-phenylene-diamine and 0.4 mM $H_2O_2$ in 100 mM Na citrate, pH 5.0. After addition of 100 μl 0.5M $H_2SO_4$, the absorbance at 492 nm was determined in an ELISA processor II (Hoechst Behring, Marburg, FRG). The assay was standardized with human umbilical cord EC-SOD C. EC-SOD concentrations down to ~0.25 ng/ml could be determined.

The production of EC-SOD determined with ELISA varied a lot between transgenic lines but overall highest in the WAP transgenes (Table 1). One line, #68, displayed a very high productivity, around 0.7 mg/ml.

TABLE 1

Production of human EC-SOD in milk of transgenic mice

| Vector | Transgenic line | EC-SOD (ng/ml) |
|---|---|---|
| pS172 | 65 | 90 |
|  | 66,67 | UD[a] |
|  | 68 | 710000 |
| pS315 | 90 | 15 |
| pS387 | 607,702 | UD |
|  | 716 | 8 |
| None | Control | 0–0.75 |

[a]UD, Undetectable, within the range of controls.

SDS-PAGE and Immunoblotting for the presence of human EC-SOD

SDS-gels were run in a Midget Electrophoresis Unit (Pharmacia-LKB) according to the discontinuous buffer system described by Laemmli [46]. Gels were blotted in 48 mM Tris, 39 mM glycine, 1.3 mM SDS, 20% methanol, in a Trans Blot unit (Bio-Rad, Richmond, Calif.) under constant voltage (0.8 mA/cm2). EC-SOD was detected by the use of polyclonal antibodies prepared in rabbits using the native protein for immunization and immobilized EC-SOD for affinity purification. Alkaline phosphatase anti rabbit IgG (Dakopatts, Copenhagen, Denmark) was used as secondary antibody.

Milk was analyzed by SDS/PAGE and immunoblotting for the presence of human EC-SOD (FIG. 4). With this method, human EC-SOD was detected in milk from the WAP/EC-SOD line #68, but was not detected in milk from the other lines or in milk from non-transgenic animals.

Example 6

Characterization of EC-SOD produced in transgenic mice

Native EC-SOD and recombinant EC-SOD expressed in CHO-cells was obtained from Symbicom AB (UmeA, Sweden).

Quantification of EC-SOD activity

The superoxide dismutase activity of samples was determined by a direct spectrophotometric method employing $KO_2$ [44], as slightly modified in [45]. In brief, the basis of the method is that SOD is determined in terms of its ability to catalyze the disproportionation (decay) of $O_2.^-$ in alkaline aqueous solution. At alkaline pH and low $O_2^-$ concentration, the $O_2.^-$ radical is stable enough to be studied in common UV-vis spectrophotometers, using the broad absorbance maximum at 245–250 nm. Thus the assay was conducted at pH 9.5 and the disproportionation studied directly in a spectrophotometer. One unit in the assay is defined as the activity that brings about a disproportionation of $O_2.^-$ at a rate of 0.1 sec-1 in 3 ml of buffer. Under these conditions, one unit of enzyme corresponds to 8.6 ng native or recombinant human EC-SOD C [13].

This assay is 40 times more sensitive (i.e. the units correspond to 40 times less enzyme) than the original xanthine oxidase—cytochrome C assay [9].

Results

The SOD activity of control milk was about a hundred U/ml, why enhancements in activity in the milk samples with low EC-SOD production not could be distinguished with certainty. However, in line #68 the SOD activity in the milk was very high (FIG. 5), and the specific activity (U/ng EC-SOD) was apparently identical to that of native and CHO-produced recombinant EC-SOD [13]. Production of recombinant EC-SOD was stable throughout lactation.

Determination of apparent molecular masses by means of size exclusion chromatography Apparent molecular weight of EC-SOD was determined by gel chromatography, at 4° C. using a LKB HPLC apparatus (Pharmacia LKB Biotechnology Inc.). The samples containing human EC-SOD variants were applied to a Sepharyl S-300 column (Pharmacia LKB Biotechnology Inc.) (1.6×89 cm), equilibrated and eluted with 10 mM potassium phosphate, pH 7.4, containing 0.15M NaCl, at a flow rate of 19.8 ml per hour. The effluent was collected in 1.35 ml fractions and the EC-SOD content determined by ELISA as described above. The column was calibrated with IgG 156 (kDa) (Sigma Chemical Co., St. Louis, USA), bovine serum albumin (67 kDa) (Sigma Chemical Co., St. Louis, USA) and carbonic anhydrase (29 kDa) (Sigma Chemical Co., St. Louis, USA). The calibration curve was constructed by means of plotting the log molecular weights of the calibrators versus their elution volumes.

The EC-SOD produced in milk from transgenic mice eluted from Sephacryl S-300 size exclusion chromatography column at a position corresponding to the molecular mass 155 kDa (data not shown). The apparent molecular mass of the recombinant EC-SOD subunit from mouse milk was similar to CHO produced recombinant EC-SOD. Some minor discrepancies were observed. Native EC-SOD of human plasma, and recombinant CHO-produced EC-SOD, chromatographed in parallel, eluted at virtually identical elution volumes. Recombinant EC-SOD from transgenic mice showed approximately 5% protein of higher mers than tetramers. This value is close to that of native human EC-SOD but considerably lower than that of recombinant EC-SOD from CHO cells [47]. The relative amount of dimers was higher in milk derived EC-SOD (FIG. 4). The proportion of the multimers also increased in samples from the later stages of lactation.

Glycosylation pattern.

Recombinant EC-SOD produced by CHO cells and mouse mammary glands and native human EC-SOD were stained by PAS and found to contain oxidizible carbohydrate moieties. A characterization of the glycans was made by analyzing the lectin binding properties (Table 2).

The binding of the different SODs to lectins was analyzed using the lectin-link kit (Gebzyme, Cambridge, Mass.). This contained the following biotinylated lectins: Concavalin A (conA), wheat germ agglutinatinin (WGA), *Ricinus communis* agglutinin (RCA), *Datura stramonium* agglutinin (DSA) and *Sambucus nigra* agglutinin (SNA). The proteins were first run on SDS-PAGE and thereafter electroblotted and developed using the different lectins.

Both CHO and mouse milk derived recombinant EC-SOD bound RCA weaker than the native protein. This indicates that the native protein may contain terminal galactose which are absent or blocked by sialic acid in the recombinant proteins. The three EC-SODs differ with respect to SNA binding. Only milk derived recombinant EC-SOD was found to bind this lectin, indicating that EC-SOD produced in transgenic mice has terminal sialic acid residue(s) attached to galactose in a2,6 (or a2,3) position.

TABLE 2

Lectin binding of native and recombinant human EC-SOD
Comparison of the lectin binding properties of native human umbilical cord EC-SOD (n EC-SOD), recombinant EC-SOD produced in CHO cells (CHO EC-SOD) and EC-SOD produced in milk from transgenic mice (TG EC-SOD). The binding is divided into four different strengths: no (−), weak (+), medium (++), and strong (+++). The lectins are abbreviated as described in materials and methods.

|  | RCA | ConA | SNA | DSA | WGA |
|---|---|---|---|---|---|
| n EC-SOD | +++ | ++ | − | + | − |
| CHO EC-SOD | + | +++ | − | ++ | + |
| TG EC-SOD | + | ++ | ++ | + | ++ |

Plasma clearance of EC-SOD in rabbits

Recombinant EC-SOD from mouse milk was partially purified by chromatography on Heparin-Sepharose equilibrated with 50 mm Na phosphate, pH 7.4. Sound EC-SOD was eluted with a gradient of NaCl in the same buffer. The central ⅔ of the high heparin-affinity fraction (cf. FIG. 6) was collected and used for plasma clearance studies. About 10 μg of EC-SOD per kg body weight, dissolved in 50 mM potassium phosphate, pH 7.4, containing 0.2% bovine serum albumin, was injected into ear veins of chinchilla ram rabbits, weights 3–4 kg. Blood samples were tapped at times indicated in FIG. 7 into tubes containing EDTA as an anti-coagulant. The experiments were terminated at 1, 6 or 24 h, cf. FIG. 7, by intravenous injection of heparin, 2500 IU/kg body weight, followed by tapping of blood samples at 2, 5 and 15 min thereafter. The plasma volumes varied between 34 and 38 ml/kg body weight. The rabbits were used only once.

After intravenous injection milk derived recombinant EC-SOD was rapidly, to about 97%, sequestered from the blood plasma (FIG. 7). This sequestering is apparently due to binding to heparan sulphate proteoglycan in the glycocalyx of endothelial cell surfaces [3, 4, 15, 17, 18]. The decline thereafter was slow. Injection of large doses of heparin at 1, 5 and 24 hours lead to prompt release of the enzymes to plasma. This behaviour is very similar to that previously found with CHO produced recombinant EC-SOD.

However, CHO produced EC-SOD displayed a somewhat slower elimination from the circulation.

Analytical separation of EC-SOD on Heparin-Sepharose

EC-SOD was separated by Heparin-Sepharose chromatography using a Pharmacia FPLC apparatus, at room temperature. The columns contained 1 ml Heparin-Sepharose (Pharmacia Laboratory Separation Division, Uppsala, Sweden) with 15 mM Na cacodylate/50 mM NaCl, pH 6.50, as equilibration buffer and eluent. The absorbance at 280 nm was monitored on the eluent. The samples were applied at 5 ml per hour and when the absorbance at 280 nm approached the baseline, bound components were eluted with a linear gradient of NaCl in the buffer (0–1 mol/l) at 9 ml/h. The effluent was collected in 0.65 ml fractions and EC-SOD determined by enzyme-linked immunosorbent assay (ELISA), which method is described below. The chloride content of EC-SOD was determined using a standard chloride titrator (American Instrument Co, Inc, Md, USA).

Before application the solvents of the culture media were exchanged to 15 mM sodium cacodylate/50 mM NaCl, pH 6.50, on a Filtron Omega cell membrane concentration system. In general 1–2 ml of culture medium was applied to the Heparin-Sepharose® column.

Upon chromatography on Heparin Sepharose milk derived recombinant EC-SOD produced in transgenic mice displays a major peak eluting at about 0.54 m NaCl, a concentration identical to that seen with native and CHO produced recombinant EC-SOD [19], (FIG. 7). There was, however, some material with reduced and aberrant heparin affinity.

The recombinant EC-SOD produced in milk was apparently structurally identical to the previously studied native plasma and CHO-produced recombinant human EC-SODs. The apparent molecular masses were indistinguishable upon gel exclusion chromatography as were the subunits upon SDS/PAGE-immunoblotting. The specific enzymic activity was virtually identical to those of native and CHO-produced recombinant EC-SOD. The major part of the milk produced EC-SOD displayed a heparin affinity identical to that of the previously studied EC-SODs. The heparin-binding domain of EC-SOD is highly susceptible to proteolytic truncation [20]. The present investigation indicated that only minor such cleavage occurred despite the presence of proteolytic activity in mouse milk [50].

As judged from the lectin-affinity investigation, there were differences in the oligosaccharide moieties between all the studied human EC-SOD types, native enzyme from umbilical cords, and recombinant produced by CHO cells and mouse mammary glands. However, the finding does not necessarily indicate that the recombinant EC-SOD's contain oligosaccharide moieties that do not exist bound to EC-SOD in the human body. The oligosaccharides are known to be heterogeneous, even as produced by a single cell type [51]. The umbilical cord native EC-SOD studied is probably mainly produced by fibroblast. However, EC-SOD is also secreted by glia cells [521, smooth muscle cells (unpublished) and possibly other not yet identified cell types. It is well known that the glycosylation of a protein may vary widely when it is produced by different cell types in the human body [53].

Finally, the recombinant EC-SOD from mouse milk was found to behave similarly to native and recombinant CHO-produced EC-SOD [15, 18] after intravenous injection into rabbits.

There was a prompt binding to the vascular endothelium as well as a rapid release after injection of heparin. Possibly, the mouse milk produced EC-SOD was a little more rapidly eliminated from the circulation than the previously studied forms.

Example 7

Cloning, sequencing and organization of genomic human EC-SOD DNA

The human EC-SOD gene is identified and isolated from a human genomic library.

Recombinant phages containing EC-SOD genomic sequences are identified by hybridization to $^{32}$P-labelled EC-SOD cDNA fragments. These labelled EC-SOD sequences that are used as probes are the entire EC-SOD cDNA, and in addition, isolated fragments from both the 5'- and 3'- end of the EC-SOD cDNA. The use of these probes in various combinations allows the identification of the recombinant EC-SOD phages that contain the entire transcribed region. This analysis of the recombinant phages and the EC-SOD gene is even more refined using various combinations of synthetic oligonucleotides as primers in polymerase chain reaction experiments.

Identified recombinant phages containing the transcribed region of the human EC-SOD gene are plaque purified. DNA is prepared from the purified phages and the EC-SOD genomic sequences are isolated by restriction enzyme digestion and agarose electrophoresis.The EC-SOD fragments are cloned into pUC plasmids for more detailed restriction mapping, PCR analysis and sequence analysis.

The result shows that EC-SOD has at least one intron preceding the EC-SOD open reading frame. The EC-SOD open reading frame is continuous in one exon.

To achieve high production of recombinant human EC-SOD in milk from transgenic animals the transcribed intron containing part of the human EC-SOD gene is inserted in a vector, under transcriptional control of mammary epithelial cell specific regulatory sequences derived from a milk protein gene. Transgenic animals harbouring this recombinant gene are generated and identified as described above.

Example 8

In vitro maturation, fertilization and culture of bovine oocytes

Immature oocytes are obtained in large quantity (400–600/day) by aspirating follicles of ovaries obtained at abattoirs. Immature oocytes are cultured for a period in vitro before they are competent to be fertilized. Once "matured", oocytes are fertilized with sperm which has also been matured, or "capacitated" in vitro. The pronuclei of the fertilized oocyte is then injected with the transgene coding for the expression and secretion of human EC-SOD. Zygotes resulting from this in vitro fertilization and microinjection are then cultured to the late morula or blastocyst stage (5–6 days) in medium prepared, or "conditioned" by oviductal tissue. Blastocysts are then transferred non-surgically to recipient bovine species for the balance of gestation or analyzed for integration of the transgene as described herein.

In vitro maturation (IVM)

Ovaries are obtained immediately after slaughter at local abattoirs and oocytes are recovered. Alternatively, oocytes are obtained from living bovine species by surgical, endoscopic, or transvaginal ultrasonic approaches. In all cases, oocytes are aspirated from ovarian follicles (2–10 mm diameter). After washing, oocytes are placed in a maturation medium such as a medium consisting of M199 supplemented with 10% fetal calf serum, and incubated for 24 hours at 39° C. [72].

In vitro fertilization (IVF)

Matured oocytes are fertilized with either fresh or thawed sperm. Sperm is prepared for fertilization by first obtaining a population of sperm enriched for motility by a "swim-up" separation technique [73]. Motile sperm is then added to a fertilization medium, consisting of a modified Tyrode's solution [73] supplemented with heparin to induce sperm capacitation [74]. Capacitation constitutes the final sperm maturation process which is essential for fertilization. Sperm and oocytes are co-cultured for 18 hours. A useful feature of this IVF method is that (in the case of frozen sperm) consistent, repeatable results are obtained once optimal fertilization conditions for a particular ejaculate have been defined [73].

In vitro culture (IVC)

Conventional culture systems, which support development of murine, rabbit, or human ova, do not support development of bovine embryos past the 8–16 cell stage. This problem has been overcome by pre-conditioning culture media with oviductal tissue. Oviduct-conditioned medium will support bovine embryos past the 8–16 cell stage to the blastocyst stage in vitro [62].

Bovine embryos did not yield to attempts to culture them in vitro past the 8–16 cell "block" until Camous et al. [63] demonstrated cleavage to 216 cells when embryos were co-cultured with trophoblastic tissue.

The co-culture procedure was extended to oviductal tissue, based on the ability of homo- or hetero-oviducts to support development from zygote to blastocyst. Thus, bovine embryos co-cultured with oviductal tissue, or in medium conditioned by oviductal tissue, developed from zygote to blastocyst in vitro [62, 75]. Blastocysts have been produced in this system after superovulation and artificial insemination, or by in vitro maturation (IVM), and fertilization (IVF) of immature oocytes. Blastocysts produced in this fashion resulted in pregnancies and live calves after transfer to recipient animals. The results obtained were as follows:

| Step | Efficiency (%) | Number (per 100) |
|---|---|---|
| IVM | 90 | 90 |
| IVF | 80 | 72 |
| IVC | 30 | 22 |
| Embryo transfer (% pregnant) | 50 | 11 |

Therefore, from an initial daily harvest of 500 oocytes, it is expected that approximately 55 pregnancies will result.
Preparation of oviduct tissue
Co-culture and conditioned medium
 1. Obtain oviducts after slaughter or by salpingectomy.
 2. Harvest lumenal tissue by scraping intact oviduct gently with a glass slide.
 3. Wash tissue 5 times in 10 ml modified tyrodes-hepes solution [74].
 4. Resuspend final tissue pellet in M199+10% fetal calf serum at a ratio of 1 volume tissue:50 volumes of media.
 5. Tissue suspension can be used for embryo co-culture.
 6. Alternatively, media may be conditioned for 48 hours; after centrifuging the suspension, the supernatant may be used as embryo culture medium. Conditioned medium may be stored at −70° C., if desired. Conditioned medium should be used at full strength for embryo culture (no dilution) [75].

Example 9

Generation of transgenic rabbits

Non-superovulated female rabbits are egg-donors. 19.5 hours after mating the eggs are flushed from their oviducts. An average of 8–10 eggs per donor are recovered. The eggs are analyzed for being morphologically intact, fertilized and revealing clearly a visible pronucleus. About 70 to 80% are found to be usable for microinjection.
Injection One or more of the transgene coding for the expression and secretion of human EC-SOD is/are then injected into the pronuclei of the fertilized eggs. Successful pronuclear injection are monitored by the swelling of the pronucleus.

After injection, the eggs are cultivated for several hours until the majority reach the two cell stage.

Flushing, culturing and injection are carried out in a medium consisting of phosphate-buffered saline (PBS) supplemented with calf serum.
Transference of transgenic eggs The recipient animals are virgin foster mothers which have been synchronised with the donor animals by a single i.m. injection of FSH releasing hormone. Between 8 and 10 eggs are transferred surgically in general anaesthesia to the oviducts of the pseudopregnant foster mothers. The abdominal cavity may be opened by flank incisions on both sides and the eggs transferred into the oviducts in 10 μl of the culture medium.

The virgin foster mothers are between 4 and 12 months.

The percentage of pregnancies of the recipient animals are about 60 percent which corresponds to the pregnancy rate observed in natural matings.

The transgenic animals are identified by Southern blot hybridisation of DNA extracted from ear biopsies of the newborn rabbits. The overall frequency of transgenic rabbits among newborns is about 9.5%.

All of the fertile transgenic animals are mated at an age of 3.5 months and are found to transmit the transgene to their progeny in a Mendelian fashion.

REFERENCES

1. Marklund, S. L. (1982) *Proc. Natl. Acad. Sci. USA* 79, 7634–7638.
2. Marklund, S. L., Holme, E. and Hellner, L. (1982) *Clin. Chim. Acta* 126, 41–51.
3. Karlsson, K. and Marklund, S. L. (1987) *Biochem. J.* 242, 55–59.
4. Karlsson, K. and Marklund, S. L. (1988) *Biochem. J.* 255, 223–228.
5. Marklund, S. L., Bjelle, A. and Elmqvist, L.-G. (1986) *Ann. Rheum. Dis.* 45, 847–851.
6. Marklund, S. L. (1984) *J. Clin. Invest.* 74, 1398–1403.
7. Marklund, S. L. (1984) *Biochem. J.* 222, 649–655.
8. Sandstrom, J., Karlsson, K., Edlund, T. and Marklund, S. L. (1993) *Biochem. J. In.,* 294, 853–857
9. McCord, J. M. and Fridovich, I. (1969) *J. Biol. Chem.* 244, 6049–6055.
10. Keele, B. B., McCord, J. M. and Fridovich, I. (1970) *J. Biol. Chem.* 245, 6170–6181
11. Weisiger, R. A. and Fridovich, I. (1973) *J. Biol. Chem.* 248, 4793–4796.
12. Hjalmarsson, K., Marklund, S. L., Engstrom, A. and Edlund, T. (1987) *Proc. Natl. Acad. Sci. USA* 84, 6340–6344.
13. Tibell, L., Hjalmarsson, K., Edlund, T., Skogman, G., Engstrom, A. and Marklund, S. L. (1987) *Proc. Natl. Acad. Sci. USA* 84, 6634–6638.
14. Stromqvist, M., Holgersson, J. and Samuelsson, S. (1991) *J. Chromatogr.* 548, 293–301.
15. Karlsson, K. and Marklund, S. L. (1988) *J. Clin Invest.* 82, 762–766.
16. Karlsson, K., Lindahl, U. and Marklund, S. L. (1988) *Biochem. J.* 256, 29–33.
17. Marklund, S. L. and Karlsson, K. (1989) *Lab. Invest.* 60, 659–666.
18. Karlsson, K., Edlund T., Sandstrom, J., Edlund, A. and Marklund, S. L. (1993) *Free Radic. Biol. Med.* 14, 185–190.
19. Sandstrom, J. M., Carlsson, L., Marklund, S. L. and Edlund, T. (1992) *J. Biol. Chem.* 267, 18205–18209.
20. Karlsson, K., Edlund, A., Sandstrom, J. and Marklund, S. L. (1993) *Biochem. J.* 290, 623–626.
21. Ferrari, R., Ceconi, C., Curello, S., Ghielmi, S. and Albertini, A. (1989) *Pharmacol. Res.* 21, 57–65.
22. Schoenberg, M. H. and Beger, H. G. (1990) *Chem. Biol. Interact.* 76, 141–161.
23. Sanfey, H., Bulkley, G. B. and Cameron, J. L. (1984) *Ann. Surg.* 200, 405–412.
24. Bannister, J. V., Bannister, W. H. and Rotilio, G. (1987) *CRC Crit. Rev. Biochem.* 22, 111–179.
25. Omar, B. A., Flores, S. C. and McCord, J. M. (1992) *Advances Pharmacol.* 23, 109–161.
26. Johansson, M., Deinum, J., Marklund, S. L. and Sjoquist, P.-O. (1990) *Cardiovasc. Res.* 24, 500–503.
27. Erlansson, M., Bergqvist, D., Marklund, S. L., Persson, N. H. and Svensjo, E. (1990) *Free Radic. Biol. Med.* 9, 59–65.

28. Sjoquist, P.-O., Carlsson, L., Jonasson, G., Marklund, S. L. and Abrahamsson, T. (1991) *J. Cardiovasc. Pharm.* 17, 678–683.

29. Sjoquist, P.-O. and Marklund, S. L. (1992) *Cardiovasc. Res.* 26, 347–350.

30. Abrahamsson, T., Brandt, U., Marklund/Sjoquist, P.-O. (1992) *Circ. Res.* 70, 264–271.

31. Hatori, N., Sjoquist, P.-O., Marklund, S. L., Pehrsson, S. K. and Ryden, L. (1992) *Free Radic. Biol. Med.* 13, 137–142.

32. Hatori, N., Sjoquist, P.-O., Marklund, S. L. and Ryden, L. (1992) *Free Radic. Biol. Med.* 13, 221–230.

33. Wahlund, G., Marklund, S. L. and Sjoquist, P.-O. (1992) *Free Rad. Res. Comm.* 17, 41–47.

34. Hennighausen, L. (1990) *Prot. Expr. Purif.* 1, 3–8.

35. Hennighausen, L., Ruiz, L. and Wall, R. (1990) *Curr. Opinion Biotech.* 1, 74–78.

36. Wilmut, A., Archibald, A. L., McClenaghan, M., Simons, J. P., Whitelaw, C. B. A. and Clark, A. J. (1991) *Experientia* 47, 905–912.

37. Simons, J. P., McClenaghan, M. and Clark, A. J. (1987) *Nature* 328, 530–532.

38. Wall, R. J., Pursel, V. G., Shamay, A., McKnight, R. A., Pittius, C. W. and Hennighausen, L. (1991) *Proc. Natl. Acad. Sci. USA* 88, 1701–1705.

39. Campbell, S. M., Rosen, J. M., Hennighausen, L. G., Strech-Jurk, U. and Sippel, A. E. (1984) *Nucl. Acid Res.* 12, 8685–8697.

40. Harris, S., Ali, S., Anderson, S., Archibald, A. L. and Clark, A. J. (1988) *Nucl. Acid Res.* 16, 10379–10380.

41. Hogan, B., Constantini, F. and Lacy, E. (1986) in *Manipulating the mouse embryo. A Laboratory Manual.* Cold Spring Harbor Laboratory Press, Cold Spring Harbor, N.Y.

42. Current Protocols in Molecular Biology (1992) (Ausubel, F. M., Brent, R., Kingston, R. E., Moore, D.D., Seidman, J. G., Smith, J.A., Struhl, K. eds.) John Wiley & Sons, New York, N.Y.

43. Bradford, M. M. (1976) *Anal. Biocbem.* 72, 248–254.

44. Marklund, S. L. (1976) *J. Biol. Chem.* 251, 7504–7507.

45. Marklund, S. L. (1985) in *Handbook of Methods for Oxygen Radical Research* (Greenwald, R. A. ed.) pp. 249255, CRC Press Boca Raton, Fla.

46. Laemmli, U. K. (1970) *Nature* 227, 680–685.

47. Stromqvist, M. (1993) *J. Chromatogr.* 621, 139–148

48. Palmiter, R. D. and Brinster, R. L. (1986) *Annu. Rev. Genet.* 20, 465–499.

49. Pittius, W. C., Hennighausen, L., Lee, E., Westphal, H., Nicols, E., Vitale, J. and Gordon, K. (1988) *Proc. Natl. Acad. Sci. USA* 85, 5874–5878.

50. Wilkins, T. D. and Velander, W. (1992) *J. Cell. Biochem.* 49, 333–338.

51. Rademacher, R. W., Parekh, R. B. and Dwek, R. A. (1988) *Ann. Rev. Biochem.* 57, 785–838.

52. Marklund, S. L. (1990) *Biochem. J.* 266, 213–219.

53. Moss, D. W. and Whitaker, K. B. (1985) *Enzyme* 34, 212–216.

54. Oury, T. D., Ho, Y.-S., Piantadosi, C. A. and Crapo, J. D *Proc. Natl. Acad. Sci. USA,* 89, 9715–9719

55. Rubnitz, J. and Subramani, S. (1984) *Mol. Cell. Biol.* 4, 2253–2258

56. Brinster, R. L., Allen, J. M., Behringer, R. R., Gelinas, R. E. and Palmiter, R. D. (1988) Introns increase transcriptional efficiency in transgenic mice. *Proc. Natl. Acad. Sci. USA* 85, 836–840

57. Jaenisch, R. (1976) *Proc. Natl. Acad. Sci. USA* 73, 1260–1264

58. Gordon et al. (1984) *Methods in Enzymology,* 101, 414

59. Hammer et al. (1985) *Nature,* 315, 680

60. Gandolfi et al. (1987) *J. Reprod. Fert.* 81, 23–28

61. Rexroad et al. (1988) *J. Anim. Sci.* 66, 947–953

62. Eyestone, W. H. et al. (1989) *J. Reprod. Fert.* 85, 715–720

63. Camous et al. (1984) *J. Reprod. Fert.* 72, 779–785

64. Heyman, Y. et al. (1987) *Theriogenology* 27, 5968

65. Williams et al. (1984) *Theriogenology* 22, 521–531

66. Prather et al. (1987) *Biol. Reprod.* 37, 859–866

67. Roble et al. (1987) *J. Anim. Sci.* 64, 642–664

68. Bongso et al. (1975) *Vet. Res.* 96, 124–126;

69. Rumsey et al. (1974) *J. Anim. Sci.* 39, 386–391

70. Sambrook, J., Fritsch, E. F. and Maniatis, T. E. Molecular Cloning, a laboratory manual. 2nd ed., Cold Spring Harbor Laboratory Press, 1989

71. Ausubel, F. M., Brent, R., Kingston, R. E., Moore, D. D., Seidman, J. G., Smith, J. A., Struhl, K. (eds.), Current Protocols in Molecular Biology, John Wiley & Sons, N.Y., 1991

72. Sirard et al. (1988) *Biol. Reprod.* 39, 546–552).

73. Parrish et al. (1986) *Theriogenology* 25, 591–600

74. Parrish et al. (1988) *Biol. Reprod.* 38, 1171–1180

75. Eyestone, W. H. (1989) "Factors affecting the development of early bovine embryos in vivo and in vitro." Ph.D. Thesis, University of Wisconsin

I claim:

1. A transgenic nonhuman mammal whose genome comprises an expression system, said expression system comprising
   (I) a DNA sequence encoding a mature polypeptide which dismutates superoxide radicals and binds heparin, where said DNA sequence is
   (a) the bases 1 to 666 of the DNA sequence of SEQ ID NO:1,
   (b) a DNA sequence which hybridizes to the complement of the DNA sequence of (a) above under stringent hybridization conditions carried out at 67° in 2×SSC with final washing at 67° in 1×SSC,
   (c) a DNA sequence which encodes the same amino acid sequence as that encoded by the DNA sequence of (a) or (b) above,
   (d) a DNA sequence encoding a mature polypeptide comprising a first amino acid sequence which is identical to residues 1–220 of SEQ ID NO:2 or which differs from residues 1–216 of SEQ ID NO:2 solely by one or more conservative amino acid substitutions, or
   (e) a DNA sequence encoding a polypeptide comprising a first amino acid sequence which is identical to residues 1–216 of SEQ ID NO:2, or differs therefrom solely by substitution of alanine at one or more of residues 216, 218, 219, or 220, where said polypeptide dismutates superoxide radicals and binds heparin;
   (II) a second DNA sequence which is a secretion signal sequence preceding and operably linked to (I), said signal sequence encoding a signal peptide, whereby said mature polypeptide is secreted of detectable levels into milk by said mammary gland cells; and
   (III) a regulatory element of a gene encoding a milk protein of a mammal operably linked to the DNA sequences of (I) and (II) above so as to form a hybrid gene which is expressible in the mammary gland of an adult lactating female of a non-human mammal whose genome comprises said hybrid gene; so that the mature polypeptide is secreted at detectable levels into the milk of said mammal if said mammal is a lactating female.

2. A mammal according to claim 1, wherein the regulatory element is selected from the group consisting of whey acidic protein (WAP), β-lactoglobulin and casein promoters.

3. A mammal according to claim 1, wherein the DNA sequence encoding the polypeptide is one which hybridizes with the DNA sequence shown in bases 1–666 of SEQ ID NO:1.

4. A mammal according to claim 1, wherein the DNA sequence encoding the mature polypeptide contains at least one intron sequence.

5. A mammal according to claim 1, wherein the signal peptide is selected from the group consisting of human EC-SOD signal peptide and the milk protein signal peptide.

6. A mammal according to claim 1, wherein the non-human mammal is selected from the group consisting of rabbits, mice, rats, goats, sheep, pigs, lama, camels and bovine species.

7. A mammal according to claim 1, wherein the polypeptide has a reduced heparin affinity as compared to human EC-SOD type C and is selected from the group consisting of variants T216, SAT216, SRT216, SA219, SA220, SA211–213.

8. A mammal according to claim 1, wherein the polypeptide variant has an increased heparin affinity as compared to human EC-SOD type C and is selected from the group consisting of variants SA216, SA216/218 and SA216/220.

9. The mammal of claim 1 where said mature polypeptide is able to be eluted from a heparin-sepharose column of NaCl, but only by NaCl concentrations sufficient to elute the ECSOD variant T216.

10. The mammal of claim 1 wherein the signal peptide is the signal peptide of a mammalian ECSOD.

11. The mammal of claim 1 wherein the signal peptide is the signal peptide of a milk protein.

12. The mammal of claim 1 which is a lactating female.

13. A transgenic nonhuman mammal whose genome comprises an expression system, said expression system comprising
   (I) a DNA sequence encoding a mature polypeptide comprising a first amino acid sequence which is identical to residues 1–216 of SEQ ID NO:2, or differs therefrom solely by substitution of alanine or asparagine at one or more of said residues, where said polypeptide dismutates superoxide radicals and binds heparin, and
   (II) a second DNA sequence which is a secretion signal sequence preceding and operably linked to (I), said signal sequence encoding a signal peptide, whereby said mature polypeptide is secreted at detectable levels into milk by said mammary gland cells, and
   (III) a regulatory element of a gene encoding a milk protein of a mammal operably linked to the DNA sequences of (I) and (II) above so as to form a hybrid gene which is expressible in the mammary gland of an adult female of a non-human mammal whose genome comprises said hybrid gene; so that said mature polypeptide is secreted into the milk at detectable levels of said mammal if said mammal is a lactating female, where said polypeptide dismutates superoxide radicals and binds heparin.

14. The mammal of claim 13 wherein said first amino acid sequence is identical to residues 1–216 SEQ ID NO:2.

15. The mammal of claim 13 wherein the amino acid sequence of said mature polypeptide is identical to residues 1–216 of SEQ ID NO:2.

16. The mammal of claim 13 wherein the mature polypeptide is the human ECSOD variant T216.

17. The mammal of claim 13 wherein the mature polypeptide is selected from the group consisting of human ECSOD variants SA216, SA219 and SA220.

18. The mammal of claim 13 wherein the mature polypeptide is the human ECSOD variant SAT216.

19. The mammal of claim 13 wherein the mature polypeptide is selected from the group consisting of human ECSOD variants SA216/218, SA216/220, and SA211–213.

20. The mammal of claim 13 where the substitutions if any, are all alanine substitutions.

21. The mammal of claim 20 where the substitutions are limited to one or more of residues 211–216 of SEQ ID NO:2.

22. The mammal of claim 20 where the alanine substitution, if any, is at residue 216.

23. A transgenic nonhuman mammal whose genome comprises an expression system, said expression system comprising (I) a DNA sequence encoding a mature polypeptide comprising a first amino acid sequence which is identical to residues 1–216 of SEQ ID NO:2 or which differs from residues 1–216 of SEQ ID NO:2 solely by one or more conservative amino acid substitutions;

(II) a second DNA sequence which is a secretion signal sequence preceding and operably linked to (I), said signal sequence encoding a signal peptide whereby said mature polypeptide is secreted at detectable levels into milk by said mammary gland cells, and (III) a regulatory element of a gene encoding a milk protein of a mammal operably linked to the DNA sequences of (I) and (II) above so as to form a hybrid gene which is expressible in the mammary gland of an adult female of a non-human mammal whose genome comprises said hybrid gene; so that said mature polypeptide is secreted at detectable levels into the milk of said mammal if said mammal is a lactating female, where said polypeptide dismutates superoxide radicals and binds heparin.

24. A transgenic nonhuman mammal whose genome comprises an expression system, said expression system comprising (a) a DNA sequence encoding a mature polypeptide which dismutates superoxide radicals and binds heparin, where said DNA sequence hybridizes to the complement of the DNA sequence of SEQ ID NO:1 under stringent hybridization conditions carried out at 67° in 2×SSC with final washing at 67° in 1×SSC, (b) a second DNA sequence which is a secretion signal sequence preceding and operably linked to (a), said signal sequence encoding a signal peptide, whereby said mature polypeptide is secreted at detectable levels into milk by said mammary gland cells, and (c) a regulatory element of a gene encoding a milk protein of a mammal operably linked to the DNA sequences of (a) and (b) above so as to form a hybrid gene which is expressible in the mammary gland of an adult female of a non-human mammal whose genome comprises said hybrid gene; so that the mature polypeptide is secreted at detectable levels into the milk of said mammal if said mammal is a lactating female.

25. A transgenic nonhuman mammal whose genome comprises an expression system, said expression system comprising (I) a DNA sequence encoding a mature polypeptide which dismutates superoxide radicals and binds heparin, where said DNA sequence is (a) the bases 1 to 666 of the DNA sequence of SEQ ID No:1, (b) a DNA sequence which hybridizes to the complement of the DNA sequence of (a) above under stringent hybridization conditions carried out at 67° in 2×SSC with final washing at 67° in 1×SSC, or (c) a DNA sequence which encodes the same amino acid sequence as that encoded by the DNA sequence of (a) or (b) above, (II) a second DNA sequence which is a secretion signal sequence preceding and operably linked to (I), said signal sequence encoding a signal peptide, whereby said mature polypeptide is secreted at detectable levels into milk by said mammary gland cells, and (III) a regulatory element of a gene encoding a milk protein of a mammal operably linked to the DNA sequences of (I) and (II) above so as to form a hybrid gene which is expressible in the mammary gland of an adult lactating female of a non-human mammal whose genome comprises said hybrid gene; so that the mature polypeptide is secreted at detectable levels into the milk of said mammal if said mammal is a lactating female.

26. A method for producing the transgenic non-human mammal of claim 1 comprising introducing into a non-human mammalian embryo at least one expression system comprising a DNA sequence encoding a mature polypeptide which dismutates superoxide radicals and binds heparin operatively linked to mammary gland expression regulatory sequences, implanting the embryo in to a female of the same species, permitting the embryo to develop to term and identifying those transgenic mammals which produce in their milk detectable quantities of a mature polypeptide which dismutates superoxide radicals and binds heparin.

27. A method according to claim 26, wherein 1–10 copies of the expression system are introduced.

28. A method according to claim 26, wherein a plurality of different expression systems are introduced and these systems express at least two different mature polypeptides which dismutate superoxide radicals and bind heparin.

29. The method of claim 26 wherein at least one expression system is introduced by microinjection.

30. A method for producing a transgenic non-human mammal which produces a polypeptide which dismutates superoxide radicals and binds heparin, which mammal secretes the polypeptide in its milk at detectable levels, the method comprising introducing into a non-human mammalian embryo an expression system comprising (I) a DNA sequence encoding a mature polypeptide which dismutates superoxide radicals and binds heparin, where said DNA sequence is (a) the bases 1 to 666 of the DNA sequence of SEQ ID NO:1, (b) a DNA sequence which hybridizes to the complement of the DNA sequence of (a) above under stringent hybridization conditions carried out at 67° in 2×SSC with final washing at 67° in 1×SSC, (c) a DNA sequence which encodes the same amino acid sequence as that encoded by the DNA sequence of (a) or (b) above, (d) a DNA sequence encoding a mature polypeptide comprising a first amino acid sequence which is identical to residues 1–216 of SEQ ID NO:2 or which differs from residues 1–216 of SEQ ID NO:2 solely by one or more conservative amino acid substitutions, or (e) a DNA sequence encoding a polypeptide comprising a first amino acid sequence which is identical to residues 1–220 of SEQ ID NO:2, or differs therefrom solely by substitution of alanine at one or more of residues 216, 218, 219, or 220, where said polypeptide dismutates superoxide radicals and binds heparin;

(II) a second DNA sequence which is a secretion signal sequence preceding and operably linked to (I), said signal sequence encoding a signal peptide, whereby said mature polypeptide is secreted at detectable levels into milk by said mammary gland cells; and (III) a regulatory element of a gene encoding a milk protein of a mammal operably linked to the DNA sequences of (I) and (II) above so as to form a hybrid gene which is expressible in the mammary gland of an adult lactating female of a non-human mammal whose genome comprises said hybrid gene; so that the mature polypeptide is secreted into the milk of said mammal if said mammal is a lactating female, such that the expression system is stably integrated into the genome of the mammal, developing the embryo to term and inducing lactation in the non-human mammal such that it secretes detectable levels of said polypeptide in its milk.

31. A method for producing a nonhuman milk comprising a non-native polypeptide which dismutates superoxide radicals and binds heparin, said method comprising providing a non-human mammal according to claim 1, husbanding the mammal in such a way that the DNA encoding the polypeptide is expressed in a mammary gland of the mammal and said polypeptide secreted at detectable levels into the milk thereof, and, collecting the milk secreted from the gland.

32. A method for producing a polypeptide which dismutates superoxide radicals and binds heparin, comprising producing a milk comprising said polypeptide by the method of claim 31 and recovering the polypeptide from said milk.

33. A method for producing a nonhuman milk comprising a non-native polypeptide which dismutates superoxide radicals and binds heparin, said method comprising providing a non-human mammal according to claim 24, husbanding the mammal in such a way that the DNA encoding the polypeptide is expressed in a mammary gland of the mammal and said polypeptide secreted into the milk thereof at detectable levels, and collecting the milk secreted from the gland.

34. A method for producing a polypeptide which dismutates superoxide radicals and binds heparin comprising producing milk comprising said polypeptide by the method of claim 33 and recovering the polypeptide from said milk.

35. A method for producing a nonhuman milk comprising a non-native polypeptide which dismutates superoxide radicals and binds heparin, said method comprising providing a non-human mammal according to claim 12, husbanding the mammal in such a way that the DNA encoding the polypeptide is expressed in a mammary gland of the mammal and said polypeptide secreted at detectable levels into the milk thereof, and collecting the milk secreted from the gland.

36. A method for producing a polypeptide which dismutates superoxide radicals and binds heparin, comprising producing milk using the method of claim 35, wherein the milk comprises a polypeptide which dismutates superoxide radicals and binds heparin and recovering the polypeptide from said milk.

* * * * *

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
      (A) LENGTH: 669 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Homo sapiens (ix) FEATURE:
      (A) NAME/KEY: CDS
      (B) LOCATION: 1..669

(ix) FEATURE:
      (A) NAME/KEY: mat_peptide
      (B) LOCATION: 1..666
      (D) OTHER INFORMATION: /product= "native EC-SOD"

(xi) SEQUENCE DESCRIPTION: SEQ ID NO: 1:

```
TGG ACG GGC GAG GAC TCG GCG GAG CCC AAC TCT GAC TCG GCG GAG TGG        48
Trp Thr Gly Glu Asp Ser Ala Glu Pro Asn Ser Asp Ser Ala Glu Trp
 1               5                  10                  15

ATC CGA GAC ATG TAC GCC AAG GTC ACG GAG ATC TGG CAG GAG GTC ATG        96
Ile Arg Asp Met Tyr Ala Lys Val Thr Glu Ile Trp Gln Glu Val Met
             20                  25                  30

CAG CGG CGG GAC GAC GAC GGC ACG CTC CAC GCC GCC TGC CAG GTG CAG       144
Gln Arg Arg Asp Asp Asp Gly Thr Leu His Ala Ala Cys Gln Val Gln
         35                  40                  45

CCG TCG GCC ACG CTG GAC GCC GCG CAG CCC CGG GTG ACC GGC GTC GTC       192
Pro Ser Ala Thr Leu Asp Ala Ala Gln Pro Arg Val Thr Gly Val Val
     50                  55                  60

CTC TTC CGG CAG CTT GCG CCC CGC GCC AAG CTC GAC GCC TTC TTC GCC       240
Leu Phe Arg Gln Leu Ala Pro Arg Ala Lys Leu Asp Ala Phe Phe Ala
 65                  70                  75                  80

CTG GAG GGC TTC CCG ACC GAG CCG AAC AGC TCC AGC CGC GCC ATC CAC       288
Leu Glu Gly Phe Pro Thr Glu Pro Asn Ser Ser Ser Arg Ala Ile His
                 85                  90                  95

GTG CAC CAG TTC GGG GAC CTG AGC CAG GGC TGC GAG TCC ACC GGG CCC       336
Val His Gln Phe Gly Asp Leu Ser Gln Gly Cys Glu Ser Thr Gly Pro
            100                 105                 110

CAC TAC AAC CCG CTG GCC GTG CCG CAC CCG CAG CAC CCG GGC GAC TTC       384
His Tyr Asn Pro Leu Ala Val Pro His Pro Gln His Pro Gly Asp Phe
        115                 120                 125

GGC AAC TTC GCG GTC CGC GAC GGC AGC CTC TGG AGG TAC CGC GCC GGC       432
Gly Asn Phe Ala Val Arg Asp Gly Ser Leu Trp Arg Tyr Arg Ala Gly
    130                 135                 140

CTG GCC GCC TCG CTC GCG GGC CCG CAC TCC ATC GTG GGC CGG GCC GTG       480
Leu Ala Ala Ser Leu Ala Gly Pro His Ser Ile Val Gly Arg Ala Val
145                 150                 155                 160

GTC GTC CAC GCT GGC GAG GAC GAC CTG GGC CGC GGC GGC AAC CAG GCC       528
Val Val His Ala Gly Glu Asp Asp Leu Gly Arg Gly Gly Asn Gln Ala
                165                 170                 175

AGC GTG GAG AAC GGG AAC GCG GGC CGG CGG CTG GCC TGC TGC GTG GTG       576
Ser Val Glu Asn Gly Asn Ala Gly Arg Arg Leu Ala Cys Cys Val Val
            180                 185                 190
```

```
GGC GTG TGC GGG CCC GGG CTC TGG GAG CGC CAG GCG CGG GAG CAC TCA        624
Gly Val Cys Gly Pro Gly Leu Trp Glu Arg Gln Ala Arg Glu His Ser
        195                 200                 205

GAG CGC AAG AAG CGG CGG CGC GAG AGC GAG TGC AAG GCC GCC TGA            669
Glu Arg Lys Lys Arg Arg Arg Glu Ser Glu Cys Lys Ala Ala
210                 215                 220
```

(2) INFORMATION FOR SEQ ID NO: 2:

(i) SEQUENCE CHARACTERISTICS:
        (A) LENGTH: 222 amino acids
        (B) TYPE: amino acid
        (D) TOPOLOGY: linear (ii) MOLECULE TYPE: protein (xi) SEQUENCE DESCRIPTION: SEQ ID NO: 2:

```
Trp Thr Gly Glu Asp Ser Ala Glu Pro Asn Ser Asp Ser Ala Glu Trp
 1               5                  10                  15

Ile Arg Asp Met Tyr Ala Lys Val Thr Glu Ile Trp Gln Glu Val Met
                20                  25                  30

Gln Arg Arg Asp Asp Asp Gly Thr Leu His Ala Ala Cys Gln Val Gln
            35                  40                  45

Pro Ser Ala Thr Leu Asp Ala Ala Gln Pro Arg Val Thr Gly Val Val
    50                  55                  60

Leu Phe Arg Gln Leu Ala Pro Arg Ala Lys Leu Asp Ala Phe Phe Ala
65                  70                  75                  80

Leu Glu Gly Phe Pro Thr Glu Pro Asn Ser Ser Arg Ala Ile His
                85                  90                  95

Val His Gln Phe Gly Asp Leu Ser Gln Gly Cys Glu Ser Thr Gly Pro
                100                 105                 110

His Tyr Asn Pro Leu Ala Val Pro His Pro Gln His Pro Gly Asp Phe
            115                 120                 125

Gly Asn Phe Ala Val Arg Asp Gly Ser Leu Trp Arg Tyr Arg Ala Gly
    130                 135                 140

Leu Ala Ala Ser Leu Ala Gly Pro His Ser Ile Val Gly Arg Ala Val
145                 150                 155                 160

Val Val His Ala Gly Glu Asp Asp Leu Gly Arg Gly Asn Gln Ala
                165                 170                 175

Ser Val Glu Asn Gly Asn Ala Gly Arg Arg Leu Ala Cys Cys Val Val
                180                 185                 190

Gly Val Cys Gly Pro Gly Leu Trp Glu Arg Gln Ala Arg Glu His Ser
                195                 200                 205

Glu Arg Lys Lys Arg Arg Arg Glu Ser Glu Cys Lys Ala Ala
                210                 215                 220
```

(2) INFORMATION FOR SEQ ID NO: 3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

CTGTGTGGCC AAGAAGGAAG TTTGT                                            25

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

GCCTGAGGAT GAGCCAAGTG                                               20

(2) INFORMATION FOR SEQ ID NO: 5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

GTCCAGCGTG GCCGACGGCT GCACCTG                                       27

(2) INFORMATION FOR SEQ ID NO: 6:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (v) FRAGMENT TYPE: C-terminal (ix) FEATURE:
        (A) NAME/KEY: CDS
        (B) LOCATION: 1..51
        (D) OTHER INFORMATION: /product= "C-terminal of native
            EC-SOD"

(xi) SEQUENCE DESCRIPTION: SEQ ID NO: 6:

CAC TCA GAG CGC AAG AAG CGG CGG CGC GAG AGC GAG TGC AAG GCC GCC     48
His Ser Glu Arg Lys Lys Arg Arg Arg Glu Ser Glu Cys Lys Ala Ala
 1               5                  10                  15

TGA                                                                 51

(2) INFORMATION FOR SEQ ID NO: 7:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 7:

His Ser Glu Arg Lys Lys Arg Arg Arg Glu Ser Glu Cys Lys Ala Ala
 1               5                  10                  15

(2) INFORMATION FOR SEQ ID NO: 8:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (v) FRAGMENT TYPE: C-terminal (ix) FEATURE:
             (A) NAME/KEY: CDS
             (B) LOCATION: 1..12
             (D) OTHER INFORMATION: /product= "C-terminal of variant
                 T209"

(xi) SEQUENCE DESCRIPTION: SEQ ID NO: 8:

```
CAC TCA GAG TGAAAGAAGC GGCGGCGCGA GAGCGAGTGC AAGGCCGCCT GA      51
His Ser Glu
  1
```

(2) INFORMATION FOR SEQ ID NO: 9:

(i) SEQUENCE CHARACTERISTICS:
             (A) LENGTH: 3 amino acids
             (B) TYPE: amino acid
             (D) TOPOLOGY: linear (ii) MOLECULE TYPE: protein (xi) SEQUENCE DESCRIPTION: SEQ ID NO: 9:

```
His Ser Glu
  1
```

(2) INFORMATION FOR SEQ ID NO: 10:

(i) SEQUENCE CHARACTERISTICS:
             (A) LENGTH: 51 base pairs
             (B) TYPE: nucleic acid
             (C) STRANDEDNESS: single
             (D) TOPOLOGY: linear (ii) MOLECULE TYPE: cDNA (v) FRAGMENT TYPE: C-terminal (ix) FEATURE:
             (A) NAME/KEY: CDS
             (B) LOCATION: 1..24
             (D) OTHER INFORMATION: /product= "C-terminal of variant
                 T213"

(xi) SEQUENCE DESCRIPTION: SEQ ID NO: 10:

```
CAC TCA GAG CGC AAG AAG CGG TGACGCGAGA GCGAGTGCAA GGCCGCCTGA     51
His Ser Glu Arg Lys Lys Arg
  1               5
```

(2) INFORMATION FOR SEQ ID NO: 11:

(i) SEQUENCE CHARACTERISTICS:
             (A) LENGTH: 7 amino acids
             (B) TYPE: amino acid
             (D) TOPOLOGY: linear (ii) MOLECULE TYPE: protein (xi) SEQUENCE DESCRIPTION: SEQ ID NO: 11:

```
His Ser Glu Arg Lys Lys Arg
  1               5
```

(2) INFORMATION FOR SEQ ID NO: 12:

(i) SEQUENCE CHARACTERISTICS:
             (A) LENGTH: 51 base pairs
             (B) TYPE: nucleic acid
             (C) STRANDEDNESS: single

```
            (D) TOPOLOGY: linear (ii) MOLECULE TYPE: cDNA (v) FRAGMENT TYPE: C-terminal (ix) FEATURE:
            (A) NAME/KEY: CDS
            (B) LOCATION: 1..30
            (D) OTHER INFORMATION: /product= "C-terminal of variant
                T215"

(xi) SEQUENCE DESCRIPTION: SEQ ID NO: 12:

CAC TCA GAG CGC AAG AAG CGG CGG CGC TAGAGCGAGT GCAAGGCCGC             47
His Ser Glu Arg Lys Lys Arg Arg Arg
  1               5

CTGA                                                                  51

(2) INFORMATION FOR SEQ ID NO: 13:

(i) SEQUENCE CHARACTERISTICS:
            (A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO: 13:

His Ser Glu Arg Lys Lys Arg Arg Arg
  1               5

(2) INFORMATION FOR SEQ ID NO: 14:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: cDNA (v) FRAGMENT TYPE: C-terminal (ix) FEATURE:
            (A) NAME/KEY: CDS
            (B) LOCATION: 1..33
            (D) OTHER INFORMATION: /product= "C-terminal of variant
                T216"

(xi) SEQUENCE DESCRIPTION: SEQ ID NO: 14:

CAC TCA GAG CGC AAG AAG CGG CGG CGC GAG TGAGAGTGCA AGGCCGCCTG A       51
His Ser Glu Arg Lys Lys Arg Arg Arg Glu
  1               5                  10

(2) INFORMATION FOR SEQ ID NO: 15:

(i) SEQUENCE CHARACTERISTICS:
            (A) LENGTH: 10 amino acids
            (B) TYPE: amino acid
            (D) TOPOLOGY: linear (ii) MOLECULE TYPE: protein (xi) SEQUENCE DESCRIPTION: SEQ ID NO: 15:

His Ser Glu Arg Lys Lys Arg Arg Arg Glu
  1               5                  10

(2) INFORMATION FOR SEQ ID NO: 16:

(i) SEQUENCE CHARACTERISTICS:
```

```
            (A) LENGTH: 51 base pairs
            (B) TYPE: nucleic acid
            (C) STRANDEDNESS: single
            (D) TOPOLOGY: linear (ii) MOLECULE TYPE: cDNA (v) FRAGMENT TYPE: C-terminal (ix) FEATURE:
            (A) NAME/KEY: CDS
            (B) LOCATION: 1..51
            (D) OTHER INFORMATION: /product= "C-terminal of variant
                SA216"

(xi) SEQUENCE DESCRIPTION: SEQ ID NO: 16:

CAC TCA GAG CGC AAG AAG CGG CGG CGC GCG AGC GAG TGC AAG GCC GCC        48
His Ser Glu Arg Lys Lys Arg Arg Arg Ala Ser Glu Cys Lys Ala Ala
 1               5                  10                  15

TGA                                                                   51

(2) INFORMATION FOR SEQ ID NO: 17:

(i) SEQUENCE CHARACTERISTICS:
            (A) LENGTH: 16 amino acids
            (B) TYPE: amino acid
            (D) TOPOLOGY: linear (ii) MOLECULE TYPE: protein (xi) SEQUENCE DESCRIPTION: SEQ ID NO: 17:

His Ser Glu Arg Lys Lys Arg Arg Arg Ala Ser Glu Cys Lys Ala Ala
 1               5                  10                  15

(2) INFORMATION FOR SEQ ID NO: 18:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: cDNA (v) FRAGMENT TYPE: C-terminal (ix) FEATURE:
            (A) NAME/KEY: CDS
            (B) LOCATION: 1..51
            (D) OTHER INFORMATION: /product= "C-terminal of variant
                SA219"

(xi) SEQUENCE DESCRIPTION: SEQ ID NO: 18:

CAC TCA GAG CGC AAG AAG CGG CGG CGC GAG AGC GAG GCC AAG GCC GCC        48
His Ser Glu Arg Lys Lys Arg Arg Arg Glu Ser Glu Ala Lys Ala Ala
 1               5                  10                  15

TGA                                                                   51

(2) INFORMATION FOR SEQ ID NO: 19:

(i) SEQUENCE CHARACTERISTICS:
            (A) LENGTH: 16 amino acids
            (B) TYPE: amino acid
            (D) TOPOLOGY: linear (ii) MOLECULE TYPE: protein (xi) SEQUENCE DESCRIPTION: SEQ ID NO: 19:

His Ser Glu Arg Lys Lys Arg Arg Arg Glu Ser Glu Ala Lys Ala Ala
 1               5                  10                  15
```

(2) INFORMATION FOR SEQ ID NO: 20:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (v) FRAGMENT TYPE: C-terminal (ix) FEATURE:
        (A) NAME/KEY: CDS
        (B) LOCATION: 1..51
        (D) OTHER INFORMATION: /product= "C-terminal of variant
            SA220"

(xi) SEQUENCE DESCRIPTION: SEQ ID NO: 20:

```
CAC TCA GAG CGC AAG AAG CGG CGG CGC GAG AGC GAG TGC GCG GCC GCC       48
His Ser Glu Arg Lys Lys Arg Arg Arg Glu Ser Glu Cys Ala Ala Ala
 1               5                  10                  15

TGA                                                                   51
```

(2) INFORMATION FOR SEQ ID NO: 21:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 21:

```
His Ser Glu Arg Lys Lys Arg Arg Arg Glu Ser Glu Cys Ala Ala Ala
 1               5                  10                  15
```

(2) INFORMATION FOR SEQ ID NO: 22:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (v) FRAGMENT TYPE: C-terminal (ix) FEATURE:
        (A) NAME/KEY: CDS
        (B) LOCATION: 1..51
        (D) OTHER INFORMATION: /product= "C-terminal of variant
            SA211-213"

(xi) SEQUENCE DESCRIPTION: SEQ ID NO: 22:

```
CAC TCA GAG CGC GCG GCG GCG CGG CGC GAG AGC GAG TGC AAG GCC GCC       48
His Ser Glu Arg Ala Ala Ala Arg Arg Glu Ser Glu Cys Lys Ala Ala
 1               5                  10                  15

TGA                                                                   51
```

(2) INFORMATION FOR SEQ ID NO: 23:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 23:

His Ser Glu Arg Ala Ala Ala Arg Arg Glu Ser Glu Cys Lys Ala Ala
 1               5                  10                  15

(2) INFORMATION FOR SEQ ID NO: 24:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (v) FRAGMENT TYPE: C-terminal (ix) FEATURE:
        (A) NAME/KEY: CDS
        (B) LOCATION: 1..51
        (D) OTHER INFORMATION: /product= "C-terminal of variant
            SA216/218"

(xi) SEQUENCE DESCRIPTION: SEQ ID NO: 24:

CAC TCA GAG CGC AAG AAG CGG CGG CGC GCG AGC GCG TGC AAG GCC GCC      48
His Ser Glu Arg Lys Lys Arg Arg Arg Ala Ser Ala Cys Lys Ala Ala
 1               5                  10                  15

TGA                                                                  51

(2) INFORMATION FOR SEQ ID NO: 25:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 25:

His Ser Glu Arg Lys Lys Arg Arg Arg Ala Ser Ala Cys Lys Ala Ala
 1               5                  10                  15

(2) INFORMATION FOR SEQ ID NO: 26:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (v) FRAGMENT TYPE: C-terminal (ix) FEATURE:
        (A) NAME/KEY: CDS
        (B) LOCATION: 1..51
        (D) OTHER INFORMATION: /product= "C-terminal of variant
            SA216/220"

(xi) SEQUENCE DESCRIPTION: SEQ ID NO: 26:

CAC TCA GAG CGC AAG AAG CGG CGG CGC GCG AGC GAG TGC GCG GCC GCC      48
His Ser Glu Arg Lys Lys Arg Arg Arg Ala Ser Glu Cys Ala Ala Ala
 1               5                  10                  15

TGA                                                                  51

(2) INFORMATION FOR SEQ ID NO: 27:

(i) SEQUENCE CHARACTERISTICS:

(A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 27:

His Ser Glu Arg Lys Lys Arg Arg Arg Ala Ser Glu Cys Ala Ala Ala
 1               5                  10                  15

(2) INFORMATION FOR SEQ ID NO: 28:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (v) FRAGMENT TYPE: C-terminal (ix) FEATURE:
        (A) NAME/KEY: CDS
        (B) LOCATION: 1..33
        (D) OTHER INFORMATION: /product= "C-terminal of variant
            SAT216"

(xi) SEQUENCE DESCRIPTION: SEQ ID NO: 28:

CAC TCA GAG CGC AAG AAG CGG CGG CGC GCG TGAGAGTGCA AGGCCGCCTG A        51
His Ser Glu Arg Lys Lys Arg Arg Arg Ala
 1               5                  10

(2) INFORMATION FOR SEQ ID NO: 29:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 29:

His Ser Glu Arg Lys Lys Arg Arg Arg Ala
 1               5                  10

(2) INFORMATION FOR SEQ ID NO: 30:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (v) FRAGMENT TYPE: C-terminal (ix) FEATURE:
        (A) NAME/KEY: CDS
        (B) LOCATION: 1..33
        (D) OTHER INFORMATION: /product= "C-terminal of variant
            SRT216"

(xi) SEQUENCE DESCRIPTION: SEQ ID NO: 30:

CAC TCA GAG CGC AAG AAG CGG CGG CGC CGG TGAGAGTGCA AGGCCGCCTG A        51
His Ser Glu Arg Lys Lys Arg Arg Arg Arg
 1               5                  10

(2) INFORMATION FOR SEQ ID NO: 31:

```
    (i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 31:

His Ser Glu Arg Lys Lys Arg Arg Arg Arg
1               5                   10
```